(12) United States Patent
Johansson

(10) Patent No.: US 6,716,589 B2
(45) Date of Patent: Apr. 6, 2004

(54) DISCORDANT HELIX STABILIZATION FOR PREVENTION OF AMYLOID FORMATION

(75) Inventor: Jan Johansson, Stockholm (SE)

(73) Assignee: AlphaBeta AB, Djursholm (SE)

( * ) Notice: Subject to any disclaimer, the term of this patent is extended or adjusted under 35 U.S.C. 154(b) by 6 days.

(21) Appl. No.: 09/988,842

(22) Filed: Nov. 19, 2001

(65) Prior Publication Data

US 2002/0143105 A1 Oct. 3, 2002

Related U.S. Application Data

(60) Provisional application No. 60/253,695, filed on Nov. 20, 2000, and provisional application No. 60/251,662, filed on Dec. 6, 2000.

(51) Int. Cl.[7] .............................................. G01N 33/53

(52) U.S. Cl. ....................................................... 435/7.2

(58) Field of Search ........................... 435/7.2; 525/54.1

(56) References Cited

FOREIGN PATENT DOCUMENTS

WO    WO 98/30229    7/1998

OTHER PUBLICATIONS

Gustafsson et al. "Amyloid fibril formation by pulmonary surfactant protein C" *FEBS Letters* 464:138–142 (1999).
Kallberg et al. "Prediction of Amyloid Fibril–forming Proteins" *The Journal of Biological Chemistry* 276(16):12945–12950 (2001).
Arnoux et al. "The crystal structure of HasA, a hemophore secreted by *Serratia marcescens*" *Nat. Struct. Biol.* 6:516–520 (1999).
Barsukov et al. "Three–dimensional structure of proteolytic fragment 163–231 of bacteriopsin determined from nuclear magnetic resonance data in solution" *Eur. J. Biochem.* 206:665–672 (1992).
Bode et al. "Structure of astacin and implications for activation of astacins and zinc–ligation of collagenases" *Nature* 358:164–167 (1992).
Booth et al. "Instability, unfolding and aggregation of human lysozyme variants underlying amyloid fibrillogenesis" *Nature* 385:787–793 (1997).
Cherfils et al. "Structure of the Sec7 domain of the Arf exchange factor ARNO" *Nature* 392:101–105 (1998).
Chiti et al. "Designing conditions for in vitro formation of amyloid protofilaments and fibrils" *Proc. Natl. Acad. Sci. USA* 96:3590–3594 (1999).
Chou et al. "Prediction of the Secondary Structure of Proteins from their Amino Acid Sequence" *Adv. Enzymol.* 47:45–148 (1978).
Dobson "Protein misfolding, evolution and disease" *TIBS* 24:329–332 (1999).

Esler et al. "Point Mutations in the Central Hyprophobic Cluster of a Human β–Amyloid Congener Disrupts Peptide Folding and Abolishes Plaque Competence" *Biochemistry* 35:13914–13921 (19960.
Gomis–Ruth et al. "Structures of adamalysin II with peptidic inhibitors. Implications for the design of tumor necrosis factor α convertase inhibitors" *Protein Sci.* 7:283–289 (1998).
James et al. "Solution structure of a 142–residue recombinant prion protein corresponding to the infectious fragment of the scrapie isoform" *Proc. Natl. Acad. Sci. USA* 94:10086–10091 (1997).
Johansson et al. "The NMR Structure of the Pulmonary Surfactant–Associated Polypeptide SP–C in an Apolar Solvent Contains a Valyl–Rich α–Helix" *Biochemistry* 33:6015–6023 (1994).
Johansson et al. "Pulmonary surfactant–associated polypeptide SP–C in lipid micelles: CD studies of intact SP–C and NMR secondary structure determination of depalmitoyl––SP–C(1–17)" *FEBS Lett.*362:261–265 (1995).
Kallberg et al. "Prediction of Amyloid Fibril–forming Proteins" *Journal of Biological Chemistry* 276:12945–12950 (2001).
Kelly et al. "2.8–A Structure of Penicillin–sensitive D–Alanyl Carboxypeptidase–transpeptidase from *Streptomyces* R61 and Complexes with β–Lactams" *J. Biol. Chem.* 260:6449–6458 (1985).
Klunk et al. "Quantifying Amyloid β–Peptide (Aβ) Aggregation Using the Congo Red–Aβ (CR–Aβ) Spectrophotometric Assay" *Anal. Biochem.* 266:66–76 (1999).
Lansbury "Evolution of amyloid: What normal protein folding may tell us about fibrillogenesis and disease" *Proc. Natl. Acad. Sci. USA* 96:3342–3344 (1999).
LeVine "Thioflavine T interaction with synthetic Alzheimer's disease β–amyloid peptides: Detection amyloid aggregation in solution" *Prot.Science* 2:404–410 (1993).
Liemann et al. "Influence of Amino Acid Substitutions Related to Inherited Human Prion Diseases on the Thermodynamic Stability of the Cellular Prion Protein" *Biochemistry* 38:3258–3267 (1999).
Mandel et al. "Identification of protein–protein interfaces by decreased amide proton solvent accessibility" *Proc. Natl. Acad. Sci. USA* 95:14705–14710 (1998).

(List continued on next page.)

*Primary Examiner*—Elizabeth Kemmerer
*Assistant Examiner*—Christopher James Nichols
(74) *Attorney, Agent, or Firm*—Fish & Richardson P.C.

(57) ABSTRACT

The invention is based on the discovery that the presence of a discordant helix in a protein or peptide is predictive of that protein or peptide's ability to form amyloid. The invention includes methods for detecting discordant helices and methods of screening for compounds that stabilize the α-helix of a discordant helix-containing polypeptide. Compounds discovered using these methods are useful for treating or preventing disorders in which amyloid is produced. Such disorders include Alzheimer's disease and prion-associated disorders.

26 Claims, 14 Drawing Sheets

OTHER PUBLICATIONS

Näslund et al. "Correlation Between Elevated Levels of Amyloid β–Peptide in the Brain and Cognitive Decline" *J. American Medical Association* 283:1571–1577 (2000).

Pramanik et al. "Electrospray Ionization Mass Spectrometry for the Study of Non–covalent Complexes: an Emerging Technology" *J. Mass Spectrom* 33:911–920 (1998).

Riek et al. "NMR structure of the mouse prion protein domain PrP(121–231)" *Nature* 382:180–182 (1996).

Rosenzweig et al. "Geometry of the soluble methane monooxygenase catalytic diiron center in two oxidation states" *Chem. Biol.* 2:409–418 (1995).

Salomon et al. "Nicotine inhibits amyloid formation by the beta–peptide" *Biochemistry* 35:13568–13578 (1996).

Selkoe "The Origins of Alzheimer Disease" *J. American Medical Association* 283:1615–1617 (2000).

Sipe "Amyloidosis" *Annu. Rev. Biochem.* 61:947–975 (1992).

Smith et al. "Probing the Non–covalent Structure of Proteins by Amide Hydrogen Exchange and Mass Spectrometry" *J. Mass Spectrom* 32:135–146 (1997).

Soto et al. "Inhibition of Alzheimer's Amyloidosis by Peptides That Prevent β–Sheet Conformation" *Biochem Biophys Res Commun* 226:672–680 (1996).

Tjernberg et al. "A Molecular Model of Alzheimer Amyloid β–Peptide Fibril Formation" *J. Biol. Chem.* 274:12619–12625 (1999).

Tjernberg et al. "Arrest of β–Amyloid Fibril Formation by a Pentapeptide Ligand" *J.Biol.Chem.* 371:8545–8548 (1996).

Vandenbussche et al. "Secondary Structure and Orientation of the Surfactant Protein SP–B in a Lipid Environment. A Fourier Transform Infrared Spectroscopy Study" *Biochemistry* 31:9169–9176 (1992).

Wang et al. "Conformation of human serum apolipoprotein A–I(166–185) in the presence of sodium dodecyl sulfate of dodecylphophocholijne by H–NMR and CD. Evidence for specific peptide–SDS interactions" *Bioghim Biophys Acta* 1301:174–184 (1996).

Zahn et al. "NMR solution structure of the human prion protein" *Proc. Natl. Acad. Sci. USA* 97:145–150 (2000).

KAD

KAD

KFFE

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 1

Lys Phe Phe Glu
  1

<210> SEQ ID NO 2
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 2

Lys Ala Ala Glu
  1

<210> SEQ ID NO 3
<211> LENGTH: 40
<212> TYPE: PRT
<213> ORGANISM: Artificial Sequence
<220> FEATURE:
<223> OTHER INFORMATION: Synthetically generated peptide

<400> SEQUENCE: 3

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
             20                  25                  30

Gly Leu Met Val Gly Gly Val Val
         35                  40

<210> SEQ ID NO 4
<211> LENGTH: 35
<212> TYPE: PRT
<213> ORGANISM: Artificial Sequence
<220> FEATURE:
<223> OTHER INFORMATION: Synthetically generated peptide

<400> SEQUENCE: 4

Ala Gly Ile Val Pro Leu Asn Ile Glu Thr Leu Leu Phe Met Val Leu
  1               5                  10                  15

Asp Val Ser Ala Lys Val Gly Phe Gly Leu Ile Leu Leu Arg Ser Arg
             20                  25                  30

Ala Ile Phe
       35
```

```
<210> SEQ ID NO 5
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 5

Asn Leu Lys Arg Leu Leu Val Val Val Val Val Val Leu Val Val
 1               5                  10                  15

Val Val Ile Val Gly Ala Leu Leu Met
            20                  25

<210> SEQ ID NO 6
<211> LENGTH: 43
<212> TYPE: PRT
<213> ORGANISM: Artificial Sequence
<220> FEATURE:
<223> OTHER INFORMATION: Synthetically generated peptide

<400> SEQUENCE: 6

Gly Gly Gly Gly Val Asp Val Gly Asp Val Val Ser Ala Ile Gln Gly
 1               5                  10                  15

Ala Ala Gly Pro Ile Ala Ala Ile Gly Gly Ala Val Leu Thr Val Met
            20                  25                  30

Val Gly Ile Lys Val Tyr Lys Trp Val Arg Arg
        35                  40

<210> SEQ ID NO 7
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 7

Gly Ser Val Thr Lys Ser Phe Ser Ala Val Val Leu Leu Gln Leu Val
 1               5                  10                  15

Asp

<210> SEQ ID NO 8
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 8

Asn Asn Phe Val His Asp Cys Val Asn Ile Thr Ile Lys Gln His Thr
 1               5                  10                  15

Val Thr Thr Thr Thr Lys
            20

<210> SEQ ID NO 9
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 9

Gln Lys Leu Val Phe Phe Ala Glu Asp Val Gly
 1               5                  10
```

<210> SEQ ID NO 10
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 10

Gln Asn Asn Phe Val His Asp Cys Val Asn Ile Thr Ile Lys Gln His
 1               5                  10                  15

Thr Val Thr Thr Thr Thr Lys
            20

<210> SEQ ID NO 11
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 11

Gln Asn Asn Phe Val His Asp Cys Val Asn Ile Thr Ile Lys Gln His
 1               5                  10                  15

Thr Val Thr Thr Thr Thr Lys
            20

<210> SEQ ID NO 12
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 12

Thr Asp Thr Cys Tyr Val Leu Ser Phe Ala Val Ile Met Leu Asn Thr
 1               5                  10                  15

Ser Leu His

<210> SEQ ID NO 13
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 13

Ile Thr Pro Thr Val Phe Leu Ser Ile Glu Thr Asp Glu Leu Arg His
 1               5                  10                  15

Met Ala Asn Gly Tyr Gln Thr Val Val Ser Ile
            20                  25

<210> SEQ ID NO 14
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 14

Gln Gly Gly Ala Val Val Phe His Thr Ala Phe Ile Asn
 1               5                  10

<210> SEQ ID NO 15

```
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 15

Tyr Ile Leu Phe Trp Asn His Val Gly Leu Glu Leu Asn Arg Val Thr
 1               5                  10                  15

His Thr Val

<210> SEQ ID NO 16
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 16

Gly Ser Leu Thr Ser Gln Phe Ser Tyr Val Val Gly Arg Ser Ala Leu
 1               5                  10                  15

Arg

<210> SEQ ID NO 17
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 17

Phe His Asp Lys Tyr Gly Asn Ala Val Leu Ala Ser Gly Ala Thr Phe
 1               5                  10                  15

Cys Val Ala Val Trp Val Tyr Met Ala Thr Gln
             20                  25

<210> SEQ ID NO 18
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 18

Ser Trp Ala Arg Ala Thr Val Val Ala Leu Ser Ile Val Met Ser Arg
 1               5                  10                  15

Gln

<210> SEQ ID NO 19
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 19

Pro Tyr Met Glu Gly Val Asn Pro Phe Ile Lys Ser Asn Lys His Arg
 1               5                  10                  15

Met Ile Met Phe Leu Asp Glu Leu Gly
             20                  25

<210> SEQ ID NO 20
<211> LENGTH: 13
<212> TYPE: PRT
```

```
<213> ORGANISM: Artificial Sequence
<220> FEATURE:
<223> OTHER INFORMATION: Synthetically generated peptide

<400> SEQUENCE: 20

Phe Trp Lys Val Phe Pro Val Arg Val Phe Arg Leu Leu
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 21

Val Val His Gln Val Val Tyr Gly Leu Met Ser
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 22

Pro Glu Ile Ile Val Gly Ile Ile Gly Val Glu Thr
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 23

Pro Ile Lys Val Ser Arg Val Gly Ser Ala Met
 1               5                  10

<210> SEQ ID NO 24
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 24

Asn Leu Lys Arg Leu Leu Leu Leu Leu Leu Leu Leu Leu Leu
 1               5                  10                  15

Leu Leu Ile Leu Gly Ala Leu Leu Met
                20                  25

<210> SEQ ID NO 25
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 25

Gln Lys Leu Val Phe Phe Ala Glu Asp Val Gly
 1               5                  10

<210> SEQ ID NO 26
```

```
-continued

<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 26

Gln Ala Ala Val Phe Ala Ala Glu Asp Val Gly
 1               5                  10
```

DISCORDANT HELIX STABILIZATION FOR PREVENTION OF AMYLOID FORMATION

CROSS-REFERENCE TO RELATED APPLICATIONS

This application is claims priority from U.S. Provisional Application Serial No. 60/253,695, filed on Nov. 20, 2000, and U.S. Provisional Application Serial No. 60/251,662, filed on Dec. 6, 2000. These applications are incorporated herein by reference in their entirety.

TECHNICAL FIELD

This invention relates to protein structure, and more particularly to proteins involved in amyloidogenic disorders.

BACKGROUND

Alzheimer's disease and spongiform encephalopathies are examples of conditions in which specific proteins transform from their native states into bundles of ordered fibrils termed amyloid. Protein concentration, point mutations, and solvent composition influence fibril formation, but a structural feature unique to amyloid-forming protein has not been detected.

Amyloid fibrils can be formed from different proteins. They are associated with neurodegenerative disorders such as Alzheimer's disease and the prion diseases (e.g., Creutzfeld-Jakob disease in humans, scrapie in sheep, and bovine spongiform encephelopathy), as well as other organ-specific and systemic amyloidoses (*The Merck Manual*, 16th ed., Merck Research Laboratories, Rahway, N.J., 1992, pp. 1052–1053; Kelly, 1996, Curr. Op. Struct. Biol. 6:11–17). The proteins involved in forming amyloid are constitutively present in a soluble state, but form insoluble aggregates under certain conditions (Chiti et al., 1999, Proc. Natl. Acad. Sci. USA 96:3590–3594). There are no obvious common properties in amino acid sequence, three dimensional structure, or function among the approximately 20 proteins that are known to be specifically associated with amyloid diseases (Sipe, 1992, Annu. Rev. Biochem. 61:947–975). In spite of the differences in native structures, the amyloid fibrils are similar, irrespective of the protein from which they originate (Dobson, 1999, TIBS 24:329–332). Amyloid fibrils are built up from a cross-β-scaffold, with β-strands perpendicular and β-sheets parallel to the fiber axis.

Amyloid diseases mostly occur without known precipitating factors (Lansbury, 1999, Proc. Natl. Acad. Sci. USA 96:3342–3344). Destabilizing point mutations can cause fibril formation of an otherwise stable protein, e.g., in lysozyme (Booth et al., 1997, Nature 385:787–793), but point mutations related to inherited forms of human prion diseases do not induce PrPSc (the disease-associated form of a prion) in vitro and are not generally destabilizing (Liemann et al., 1999, Biochemistry 38:3258–3267). The so-called Aβ (e.g., 1–42 residue) peptide associated with Alzheimer's disease is highly fibrillogenic, while peptides lacking residues 14–23 are not (Tjernberg et al., 1999, J. Biol. Chem. 274:12619–12625).

SUMMARY

The invention relates to the discovery that a polypeptide containing an amino acid sequence that is predicted to be able to undergo a conversion from α-helix to β-strand can form fibrils. An amino acid sequence that is present as a helix in a polypeptide but is predicted to form a β-strand structure is herein termed a discordant helix. Compounds that stabilize the α-helical form of a discordant helix are useful for treating disorders in which β-strand structures form fibrils. Such disorders include amyloidoses such as prion diseases and Alzheimer's disease. The invention includes methods of identifying discordant helixes, methods of identifying compounds that can stabilize the α-helical form of a discordant helix, and compounds identified by these methods. The invention also includes methods of treating disorders in which β-strand structures are a part of the pathology of the disorder, e.g., amyloidoses. Such disorders include Alzheimer's disease and prion-associated diseases (e.g., scrapie, bovine spongiform encephalopathy, and Creutzfield-Jacob disease).

The invention features a method of identifying a compound that stabilizes an α-helical conformation of a discordant helix in a polypeptide. The method includes the steps of providing a test sample containing a polypeptide that contains a discordant helix in the form of an α-helix, contacting the test sample with a test compound, and determining the rate of decrease in the amount of α-helix in the test sample, such that a lower rate of decrease in the presence of the test compound than in the absence of the test compound is an indication that the test compound stabilizes the α-helical conformation of the discordant helix in the polypeptide. The invention also includes compounds identified using this method. Test compounds that can be used according to the method include peptides, e.g., tripeptides such as dipolar tripeptides. In those embodiments where the polypeptide containing a discordant helix includes all or part of an Aβ peptide, the polypeptide can include at least residues 14–23 or 16–23 of the Aβ peptide.

The invention also feature a method of identifying a compound that can stabilize an α-helical conformation of a discordant helix-containing polypeptide in which the method includes providing a test sample comprising a polypeptide that contains a discordant helix in the form of an α-helix, contacting the test sample with a test compound for a specified amount of time, and determining the amount of α-helix present in the test sample such that a larger amount of α-helix in the presence of the test compound than in the absence of the compound indicates that the test compound stabilizes the α-helical conformation of the discordant helix in the polypeptide. The invention also includes compounds identified using this method. Test compounds that can be used according to the method include peptides, e.g., tripeptides such as dipolar tripeptides. In those embodiments where the polypeptide containing a discordant helix includes all or part of an Aβ peptide, the polypeptide can include residues 14–23 or 16–23 of the Aβ peptide.

The invention also features a method of identifying whether a protein is susceptible to forming amyloid which includes analyzing the amino acid sequence of the protein to determine whether the protein contains a predicted discordant helix, such that the presence of predicted discordant helix is an indication that the protein is susceptible to forming amyloid. The discordant helix can be at least six amino acids in length.

The invention includes a method of decreasing the rate of formation of β-strand structures between at least two discordant helix-containing polypeptides, in which the method includes contacting the discordant helix-containing polypeptides with a compound that stabilizes an α-helical form of the discordant helix. Tripeptides such as the dipolar tripeptides described herein can be used to stabilize the discordant helix.

The invention also features a method of treating an individual having or at risk for an amyloidosis. The method includes administering to the individual a therapeutically effective amount of a compound that stabilizes an α-helical form of a discordant helix-containing polypeptide that forms amyloid. The amyloidosis can be, for example, a prion disease or Alzheimer's disease. Tripeptides, e.g., dipolar tripeptides including those described herein, can be used to stabilize the discordant helix.

A "discordant helix" is an amino acid sequence that is predicted to be able to form an α-helix and is also predicted to be able to form a β-strand. A discordant helix can be identified using structure analysis programs that predict secondary structure of polypeptides, specifically by analyzing an amino acid sequence for predicted α-helix and also analyzing the amino acid sequence for predicted α-strand. A sequence that is predicted to form α-helix and β-strand is a discordant helix. A discordant helix amino acid sequence can be an isolated peptide, or form part of a polypeptide. A discordant helix can be naturally occurring in a wild type or mutant polypeptide. A discordant helix can also be in a synthetic amino acid sequence. In general, the discordant helix amino acid sequence is at least about 6 amino acids in length. Such sequences can be longer, e.g., 7, 8, 9, 10, 11, 12, 14, 16, 18, 22, 24, or 26 amino acids in length.

A "polypeptide" means a chain of amino acids regardless of length or post-translational modifications.

A "non-amyloidogenic form" of a polypeptide containing a predicted discordant helix is the form of the protein in which α-helix is the predominant conformation of the discordant amino acid sequence. Compounds that promote the α-helix conformation of a discordant helix are useful for preventing the formation of amyloid.

Unless otherwise defined, all technical and scientific terms used herein have the same meaning as commonly understood by one of ordinary skill in the art to which this invention belongs. Although methods and materials suitable for practicing the invention are described below, method and materials similar or equivalent to those described herein can be used in the practice or testing of the present invention. All publications, patent applications, patents, and other references mentioned herein are incorporated by reference. The materials, methods, and examples are illustrative only and not intended to be limiting.

Other features and advantages of the invention will be apparent from the detailed description, and from the claims.

DETAILED DESCRIPTION

Figure 1:
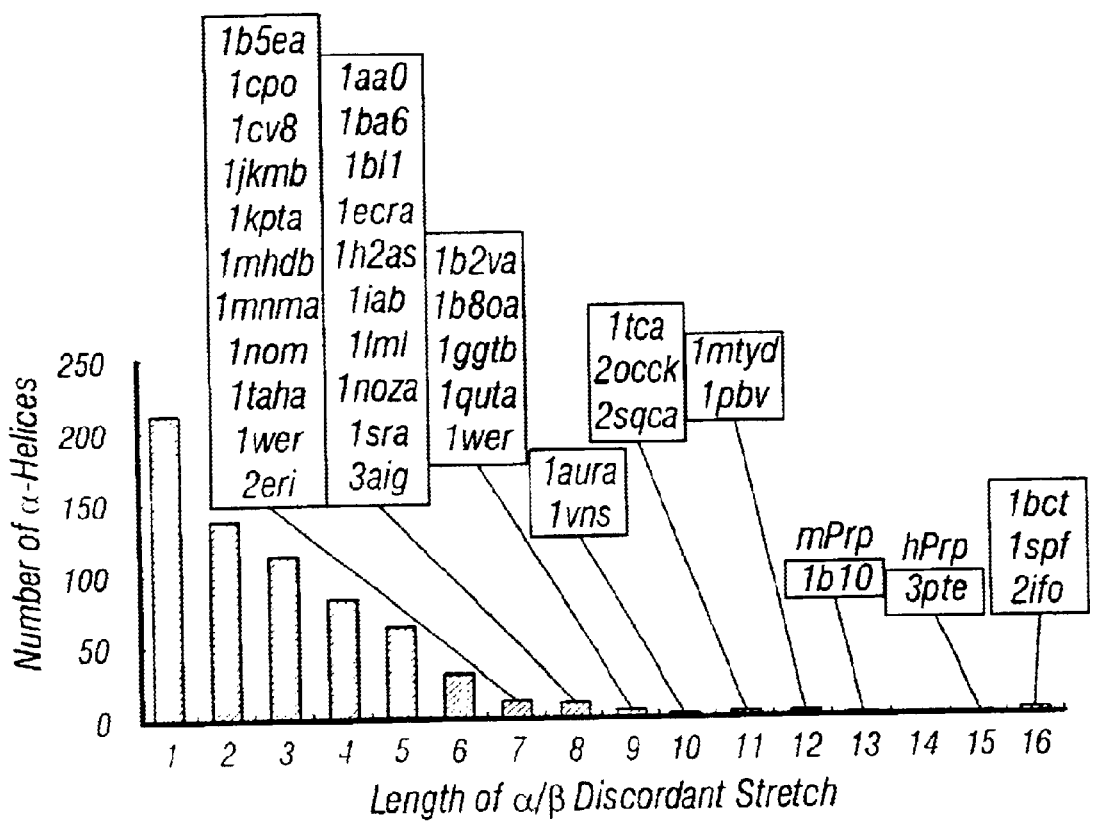
FIG. 1 is a bar graph that depicts the occurrence of α-helical segments with high β-strand propensities. The number of protein segments are plotted versus the lengths of the segments for which experimentally determined α-helices coincide with β-strands predicted with a PHD reliability index ≧5 for all residues. The PBD codes are given for the proteins from which the helices with ≧7 residues emanate. Codes in bold identify proteins that form amyloid fibrils in vivo, and italics denote proteins shown to form fibrils. The outcome of predictions for prion proteins from human (hPrP) and mouse (mPrP) are indicated. The PDB codes represent, in alphabetical order: 1aa0=fibritin deletion mutant (Bacteriophage T4), 1 aura=carboxylesterase (*Pseudomonas fluorescens*), 1b10(sPrP)=prion protein (*Syrian hamster*), 1b2va=heme-binding protein A (*Serratia marcescens*), 1b5ea=dCMP hydroxymethylase (Bacteriophage T4), 1b8oa=purine nucleoside phosphorylase (*Bos taurus*), 1ba6=beta amyloid protein (*Homo sapiens*), 1bct=bacteriorhodopsin (*Halobacterium halobium*), 1b11=parathyroid hormone receptor (*Homo sapiens*), 1 cpo=chloroperoxidase (*Leptoxyphium fumago*), 1cv8=staphopain (*Staphylococcus aureus*), 1 ecra=replication terminator protein (*Escherichia coli*), 1ggtb=coagulation factor XIII (*Homo sapiens*), 1h2as—hydrogenase (*Desulfovibrio vulgaris*), 1iab=astacin (*Astacus astacus*), 1jkmb=brefeldin A esterase (*Bacillus subtilis*), 1kpta=killer toxin (*Ustilago maydis*), 11ml=leishmanolysin (*Leishmania major*), 1mhdb=smad MH1 doman (*Homo sapiens*), 1mnma=transcription factor MVM1 (*Saccharomyces cerevisiae*), 1mtyd=methane monooxygenase (*Methylococcus capsulatus*), 1nom=DNA polymerase beta (*Rattus norvegicus*), 1noza=DNA polymerase (Bacteriophage T4), 1pbv—sec7 domain of exchange factor ARNO (*Homo sapiens*), 1quta=lytic transglycosylase Slt35 (*Escherichia coli*) 1smd=salivary amylase (*Homo sapiens*), 1spf (SP-C)=surfactant-associated protein C (*Sus scrofa*), 1sra=osteonectin (*Homo sapiens*), 1taha=lipase (*Burkholdia glumae*), 1tca=lipase B (*Candida antarctica*), 1vns=chloroperoxidase (*Curvularia inaequalis*), 1wer=Ras-GTPase-activating domain of p120GAP (*Homo sapiens*), 2erl=pheromone Er-1 (*Eurplotes raikovi*), 2ifo=inovirus (*Xanthomonas oryzae*), 2occk=cytochrome C oxidase (*Bos taurus*), 2sqca=squalene-hopene cyclase (*Alicyclobacillus acidocaldarius*), 3aig=adamalysin II (*Crotalus adamanteus*), 3pte=transpeptidase (Xstreptomyces R61).

It has been discovered that protein databanks can be screened for amyloid-forming proteins by analyzing the amino acid sequences in the databanks for proteins that harbor an α-helix in a polypeptide segment that is also predicted to form a β-strand (α-helix/β-strand discordance). In an experiment, a protein databank of 1324 non-redundant entries was searched for conflicts between experimentally determined α-helices and predicted extended structure (i.e., predicted discordant helix). This revealed a correlation between α/β discordance and ability of the corresponding protein to form amyloid fibrils under physiological conditions (Example 3). Thus, analysis of a protein's structure for α-helix/β-strand discordance can be used to predict those proteins that will form amyloid. Amyloid is believed to be associated with or responsible for the pathological changes observed during the course of amyloidoses. It follows that, inhibition or prevention of amyloid formation may prevent the occurrence or progression of these diseases. Thus, proteins containing discordant helices are useful targets for developing treatments that will prevent or ameliorate amyloidoses.

The invention includes methods of targeting discordant helix-containing segments of fibril-forming proteins (i.e., proteins that form amyloid) with ligands (termed "helix-lock molecules") that can stabilize the discordant helix region in an α-helical conformation, thereby inhibiting conversion to the β-strand conformation. Prevention of β-strand formation inhibits amyloid formation. The specific regions containing the predicted α-helix/β-strand discordance provide specific targets for drugs that can serve as such helix-lock molecules. For example, these regions can be used to screen for compounds that can be used as drugs that will prevent or inhibit conversion of the α-helix to β-strand conformation.

In experiments designed to investigate whether α-helix/β-strand discordance was likely to account for amyloid formation, a database of protein structures was screened for helical sequences predicted to form extended structures (β-structures) (Example 1). Novel proteins and polypeptide structures can be screened for the presence of predicted discordant helices. For polypeptides where experimentally derived structural data are not available, contradictory data from different secondary structure prediction programs can indicate the presence of a discordant helix (e.g., PHD analysis and Chou-Fasman analyses, Example 1).

Identification of Compounds that Stabilize α-Helical Conformation

The invention includes methods of screening for compounds that can stabilize an α-helical form of a discordant helix. The ability of a test compound to stabilize an α-helical conformation of a discordant helix is determined by measuring the amount of α-helix in a sample containing a discordant helix-containing polypeptide in the presence and absence of the particular compound. Any suitable method that detects the presence of α-helix or alternatively β-structure can be used to screen test compounds for their ability to stabilize an α-helix of a discordant helix. Such methods include NMR (e.g., Johansson et al., 1994, Biochemistry 33:6015–6023), circular dichroism (CD) (Johansson et al., 1995, FEBS Lett. 362:261–265; Wang, 1996, Biochim Biophys Acta1301:174–184), and Fourier transform infrared spectroscopy (FTIR; Vandenbussche, 1992, Biochemistry 31:9169–9176). α-Helix stability can be assessed from the rate of decrease in the amount of the α-helical form of the peptide/protein (e.g. the half-life of the α-helical form) in the presence and absence of a test compound, e.g., using electrospray (ES)-mass spectroscopy. ES or matrix-assisted laser desorption/ionisation (MALDI) mass spectrometry in combination with H/D exchange mass spectroscopy can also be used to assay for the presence of an α-helix conformation of a discordant helix. In this approach, the kinetics of disappearance of α-helix and hydrogen to deuterium (H/D) exchange of the soluble forms of a discordant helix-containing polypeptide are studied.

For relatively small proteins such as SP-C (4.2 kDa), H/D exchange rates at specific residues can be determined by NMR. However, such NMR analysis requires pure samples at high concentration, and long time periods for measurements, which make analysis of some polypeptides difficult. These problems can be partially solved by the application of mass spectrometry. Using either ES or MALDI mass spectrometry, H/D exchange levels can be monitored at low concentrations. The analysis times are short and mixtures of peptides can be analyzed. Thus, mass spectrometry is a particularly useful technique for studying the relative H/D exchange rates of protein mixtures.

Mass spectrometry is a technique that can be used to investigate non-covalent interactions involving proteins such as those involved in the formation of α-helices. To study non-covalent interactions directly using mass spectrometry, it is important that the protein be, to the extent possible, in its non-denatured state. This can be accomplished using ES as the method of ionization for the mass spectroscopy analysis. ES involves spraying the protein that is in an aqueous solution at physiological pH in the absence of an organic co-solvent (Pramanik et al., 1998, J. Mass Spectrom. 33:911–920). Highly hydrophobic proteins, such as SP-C (lung surfactant protein C), are exceptions in that their native conformations are maintained in organic solvents, and they can be sprayed when they are in methanol or chloroform/methanol/water solutions. An additional requirement for the use of ES in analysis of proteins in their native states is the careful control of the de-clustering voltage (cone voltage) within the ES interface. An excessive potential difference can lead to collision-induced dissociation or the destruction of non-covalent associations.

ES-mass Spectrometry

Mass spectrometry can be used in combination with H/D (hydrogen/deuterium) exchange to obtain information concerning non-covalent interaction and tertiary structure and stability (Smith et al., 1997, J. Mass Spectrom. 32:135–146; Mandel et al., 1998, Proc. Natl. Acad. Sci. USA 95:14705–14710). In ES-mass spectroscopy, spectra can be recorded using a quadrupole-time-of-flight (TOF) instrument (Micromass, Manchester, England). The instrument can be fitted with an orthogonal sampling nano-ES interface (Z-Spray) consisting of a quadrupole mass filter, a hexapole collision cell and an orthogonally arranged TOF analyzer complete with reflectron (Morris, 1996, Rapid Commun. Mass Spectrom. 10:889–896). Samples can be sprayed from gold-coated borosilicate capillaries (Protana A/S, Denmark). A suitable collision gas such as argon (AGA, Sweden) is used for collision-induced dissociation (CID). To determine the relative rate of disappearance from solution of various forms of a discordant helix-containing polypeptide (e.g., the disappearance of the α-helical form), an appropriate acquisition range is selected, for example, m/z 135–4000. Three hundred scans of five seconds duration are recorded for each time point and combined into one spectrum. The ion currents corresponding to the summed abundance of singly and multiply, e.g., doubly and triply protonated molecules, can be determined using maximum entropy software (Micromass). CID spectra can be recorded to confirm the structure of the polypeptide. In H/D exchange, the rates of H/D exchange reactions are monitored by continually recording ES mass spectra. At specific time points, the ions corresponding to the H/D exchanged forms of the protein of interest are subjected to CID. The location of the exchanged protons is indicated by the resultant fragmentation spectrum.

MALDI Mass Spectra

MALDI mass spectra can be recorded on a Voyager-DE™ PRO Biospectrometry Workstation (PerSeptive Biosystems Inc.) operated in the positive ion mode. Deuterated or non-deuterated polypeptide is dried on a surface (e.g., a 100 well plate) containing pre-dried α-cyano-4-hydroxycinnamic acid (20 μg), which for the recording of H/D exchange spectra was applied from a solution in $CH_3CN/D_2O$. The instrument is equipped with a 335 nm laser and operated in the linear mode employing delayed extraction. An appropriate acquisition range is used (e.g., m/z 3500–4000) and external calibration is employed (e.g., between m/z 3660.19 and 5734.58). A spectrum is calculated as an average of a number of acquisitions (e.g., 400 acquisitions), and triplicate samples are generally recorded for each time point. The number of protons exchanged with deuterons at each time point is calculated by subtracting the masses of the peptides in the protonated solvent from the masses of the peptides in the deuterated solvent. This is done, e.g., to correct for ongoing intramolecular disulfide formation. Such intramolecular disulfide formation may be observed by ES CID. In experiments to compare the rate of H/D exchange as measured by MALDI combined with ES, identical solutions are spotted on the MALDI plate and sprayed from the ES capillary.

Determination of Rate Constants from Decay Curves

Estimation of rate constant from mass spectrometric data can be done using non-linear least squares regression in Matlab® version 5.3 (Mathworks, Natick, Mass., USA) using the routines in the Mathworks Optimization Toolbox. Absolute concentrations are not available from the data, but this is not required as the helix unfolding is a first-order reaction (e.g., for SP-C, see Szyperski, 1998, Protein Sci, 7:2533–2540). Instead, ion counts can be used as the concentration unit in the non-linear regression, assuming that this measure is proportional to concentration for each peptide. Marginal standard deviations for the rate constants can be calculated by the standard procedure of linearization of the objective function (Seber et al., 1988, Non-linear Regression, John Wiley & Sons, New York)

Assay of Test Compounds

In one aspect of the invention, test compounds are assayed for their ability to stabilize an α-helical form of a discordant helix-containing polypeptide. The methods described above can be used for such assays. Typically, the test compound is added to a solution containing the polypeptide, and the content of helical structure or rate at which the α-helix form of the polypeptide disappears from the solution is determined, e.g., using CD, FTIR, NMR spectroscopy, ES-mass spectroscopy or MALDI mass spectrometry. The effects of test compounds on fibril formation can also be determined as described infra. The helical content and/or the rate of disappearance of α-helix in the presence and absence of the test compound is determined. An increased helical content and/or a decreased rate of α-helix disappearance from the solution in the presence of the test compound indicates that the test compound stabilizes the α-helix conformation of the polypeptide (i.e., is a candidate compound).

Alternatively, after incubation of a solution containing discordant helix-containing polypeptide in the presence of a test compound for a fixed time, the amount of α-helix can be determined and compared to the amount of α-helix present in the polypeptide incubated for the same amount of time in the absence of the test compound. A larger amount of α-helical form of the polypeptide in the solution containing the test compound compared to the solution that did not contain the test compound indicates that the test compound stabilizes the α-helical form of the polypeptide (i.e., is a candidate compound).

Appropriate incubation times can be determined empirically for each protein. The incubation times can be minutes, hours, days, or, in the case of discordant helix-containing proteins that form β-structures very slowly, weeks or months. Various parameters can be manipulated to modulate the rate of β-structure formation, e.g., by increasing concentration of the polypeptide or increasing the salt concentration in the solution.

Test Compounds and Candidate Compounds

Test compounds are compounds that are screened for their ability to increase the helical content of a solution containing discordant helix-containing polypeptides and/or slow the rate of conversion of the α-helix form of a discordant helix-containing polypeptide to a β-strand structure. Candidate compounds are compounds found to stabilize the α-helical form of a discordant helix-containing polypeptide. Candidate compounds can be useful for preventing the formation of β-strand structures and amyloid.

The invention provides a method for identifying compounds (e.g., polypeptides, peptidomimetics, or small molecules) that increase the stability or formation of the α-helix conformation of a discordant helix (helix-lock molecules). In general, candidate compound is a molecule that has a surface that is complementary to a surface of a discordant helix (e.g., the two surfaces are capable of an electrostatic interaction), will bind to that surface, and stabilize the helix. This will reduce the number of events in which the discordant helix converts to a β-strand conformation, thereby reducing the amount of fibril formation. Interactions between such compounds and a discordant helix can be non-covalent, in which case it is likely that complementary surfaces are required between the α-helix and the compound. The interaction between a discordant helix and a compound can also be covalent, in which case, the compound binds through a complementary interaction and then binds covalently to residue(s) of the discordant helix. A covalent interaction between the compound a discordant helix-containing protein is generally not reversible. Candidate compounds include tripeptides and tetrapeptides such as those described in the Examples. The peptides used in the screening assays can be dipolar, neutral, or mono-charged.

It is also possible to identify compounds that modify specific residues of a discordant helix so that the residues change from having a high propensity for β-strand conformation to prefer helical or random structures, thus reducing or eliminating the discordant nature of the helix. Such modifications can be introduced by modifying certain residues chemically, or by introducing mutations in the gene coding for the protein containing the discordant helix. Another method of stabilizing the α-helical form of a discordant helix is to covalently link different specific residues in a discordant helix to each other such that the helical conformation is stabilized.

Antibodies that specifically bind a discordant helix can be used to stabilize the α-helical conformation of a discordant helix. Such antibodies can be particularly useful for stabilizing the discordant helix-containing proteins that are found extracellularly or on the cell surface, although single chain recombinant antibodies can be expressed inside a cell to stabilize intracellular discordant helices. Antibodies that specifically bind to a protein containing a discordant helix can be generated using standard techniques. In general, the antibodies are recognize the α-helical form of a discordant helix or interact with a polypeptide containing a discordant helix such that the α-helix conformation is favored. Such antibodies can be made using the discordant helix-containing polypeptide or a fragment thereof, e.g., a fragment containing the discordant helix, as an antigen. Antibodies can be screened for their ability to stabilize the α-helical form of the polypeptide using the methods described herein. In general, a $F_{ab}$ fragment of an antibody is used. Antibodies useful in the invention can be polyclonal antibodies or monoclonal antibodies.

The nature of compounds that are able to stabilize the α-helical forms of peptide/proteins will depend on the amino acid sequence of the discordant peptide segment in question. One method of identifying compounds is to first use molecular modeling in silico, e.g., as implemented in the Insight/Discover program suite (Biosym/MSI, San Diego, Calif.), to identify substances that optimally fit to a specific region of a discordant helix. Identified substances are then tested for their ability to inhibit fibril formation and stabilize α-helical conformation, as described above. Another approach to identifying compounds that inhibit fibril formation and/or stabilize the α-helical form is to screen chemical libraries for molecules that inhibit fibril formation and stabilize an α-helical conformation using methods such as those described herein.

The compounds of the invention can be obtained using any of the other numerous approaches in combinatorial library methods known in the art, including biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries are known in the art, for example in DeWitt et al. (1993, Proc. Natl. Acad. Sci. USA 90:6909), Erb et al. (1994, Proc. Natl. Acad. Sci. USA 91:11422), Zuckermann et al. (1994, J. Med. Chem. 37:2678), Cho et al. (1993, Science 261:1303) Carrell et al. (1994, Angew. Chem. Int. Ed. Engl. 33:2059), Carell et al. (1994, Angew. Chem. Int. Ed. Engl. 33:2061), and Gallop et al. (1994, J. Med. Chem. 37:1233).

Libraries of compounds can be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

Additional Methods of Assaying Test Compounds
Direct Detection of Fibril Formation In some cases methods other than those that assay stabilization of α-helix conformation can be useful for the invention. For example, direct detection of fibril formation can complement the assays that measure α-helix conformation. The extent and rate of fibril formation can be measured directly by electron microscopy (EM) of fibrils formed. For example, pellets containing fibrils are suspended in a small volume of water using low energy sonication for five seconds. Aliquots of the fibril suspension are then placed on grids covered by a carbon-stabilized Formvar® film. Excess fluid is withdrawn from the grids after 30 seconds. The grids are then air-dried and negatively stained with 3% uranyl acetate in water. The stained grids are then examined and photographed in an electron microscope such as a Phillips CM120TWIN operated at 80 kV.

Fibril formation can also be assessed by staining the fibrils with dyes, e.g., Congo red or Thioflavin T, and detecting emitted light from the stained sample. For example, pellets containing fibrils are resuspended in phosphate buffered saline by sonication before addition of Congo Red (2% w/v). The samples are incubated for one hour at ambient temperature and aggregated proteins collected by centrifugation at 13,000× g for five minutes. The aggregates are then washed in water and resuspended in water. An aliquot is placed on a microscope slide, dried, and observed by polarization microscopy (e.g., using a Zeiss Axialfold microscope). Alternatively, detection of light absorption or emission at different wavelengths after staining with Congo red or Thioflavin T can be used to quantify amyloid formation (see LeVine, 1993, Prot. Science 2:404–410; Klunk et al., 1999, Anal. Biochem. 266: 266:66–76).

An assay for detection of fibril formation in the presence and absence of a test compound can be used, e.g., to prescreen test compounds for those that are to be used in subsequent assays of α-helix stabilization. Similarly, the ability of a candidate compound to inhibit fibril formation can be used to confirm the predicted efficacy of a candidate compound in preventing fibril formation.

Indirect Detection of Fibril Formation

Fibril formation can also be indirectly assayed by measuring the disappearance of the α-helical forms that, after α-helix to β-strand conversion and aggregation, give rise to fibrils. For this purpose, ES mass spectrometry is a preferred method as it distinguishes between monomeric and aggregated forms of the polypeptide that contains a discordant helix (described supra). Alternatively, aggregates can be removed, e.g., by centrifugation, and peptides remaining in solution (which are predominantly α-helical in their discordant helix region) are then quantified by techniques such as gel electrophoresis, amino acid analysis, or reversed-phase HPLC.

As with direct methods of assaying fibril formation, the indirect methods are useful for identifying compounds that interfere with α-helix to β-strand conversion and therefore will inhibit amyloid fibril formation, e.g., for screening test compounds to be used in assays for stabilization of an α-helix conformation of a discordant helix-containing polypeptide or to confirm that a candidate compound has a stabilizing effect.

The effect of different compounds on fibril formation can be observed using the above methods, preferably in combination as they have complementary profiles. Thus, staining techniques are fairly rapid, allowing screening of many compounds. Electron microscopy (EM) is more specific than dye detection since with EM the nature of the fibrils can be judged and fibrils can be quantitatively analyzed. Mass spectrometry is highly sensitive, while gel electrophoresis, amino acid analysis and reversed-phase HPLC can be used with a large number of samples but are less sensitive.

Thus, in designing screens for compounds that are useful for inhibiting fibril formation several stages of assay may be used. For example, a large number of compounds are tested using staining methods. Once an initial screen is done and a subset of the initial group of compounds are selected as candidates, ES mass spectroscopy can be used to confirm the ability of a given compound to interfere with the conversion of α-helix to β-structure in a discordant helix.

When characterizing the effects of different compounds, both the amount of fibril formed and the rates of fibril formation are of interest, since comparatively minor changes in the rates of fibril formation in vitro may reflect the tendency of a peptide/protein to form amyloid fibrils over a long time span in vivo.

Identification of Compounds that Reduce Aβ Aggregation and Fibril Formation

Discordant helices composed of residues with a high β-strand propensity are found in Aβ, PrP, and other amyloid-forming proteins. As described in Examples 4–7, dipolar tripeptides such as the KAD tripeptide reduce Aβ aggregation and fibril formation and induce the formation of short fibril fragments. The charges of the tripeptides are separated by a distance that almost perfectly matches the distance between charged residues in the discordant Aβ(16–23) α-helix. A "helix-lock" mechanism is proposed as follows in which stabilization of discordant helices by external factors can reduce fibril formation.

Experimental data and theoretical models indicate that α-helix to β-strand conversion of the 16–23 region of Aβ is critical for amyloid fibril formation. Since Aβ positions 16–23 show helical structures in the presence of membrane-mimicking solvents or detergents, it is likely that this region is also helical in membrane-associated APP. However, in liberated Aβ in an aqueous solution, a helical conformation will be only transiently stable, in line with the unordered Aβ conformation in water detected by spectroscopic methods (Serpell, 2000, Biochim. Biophys. Acta 1502:16–30). Conversion of the 16–23 region into extended/β-strand conformation is required for formation of fibrils built up from β-sheets (FIG. 12).

Figure 12:
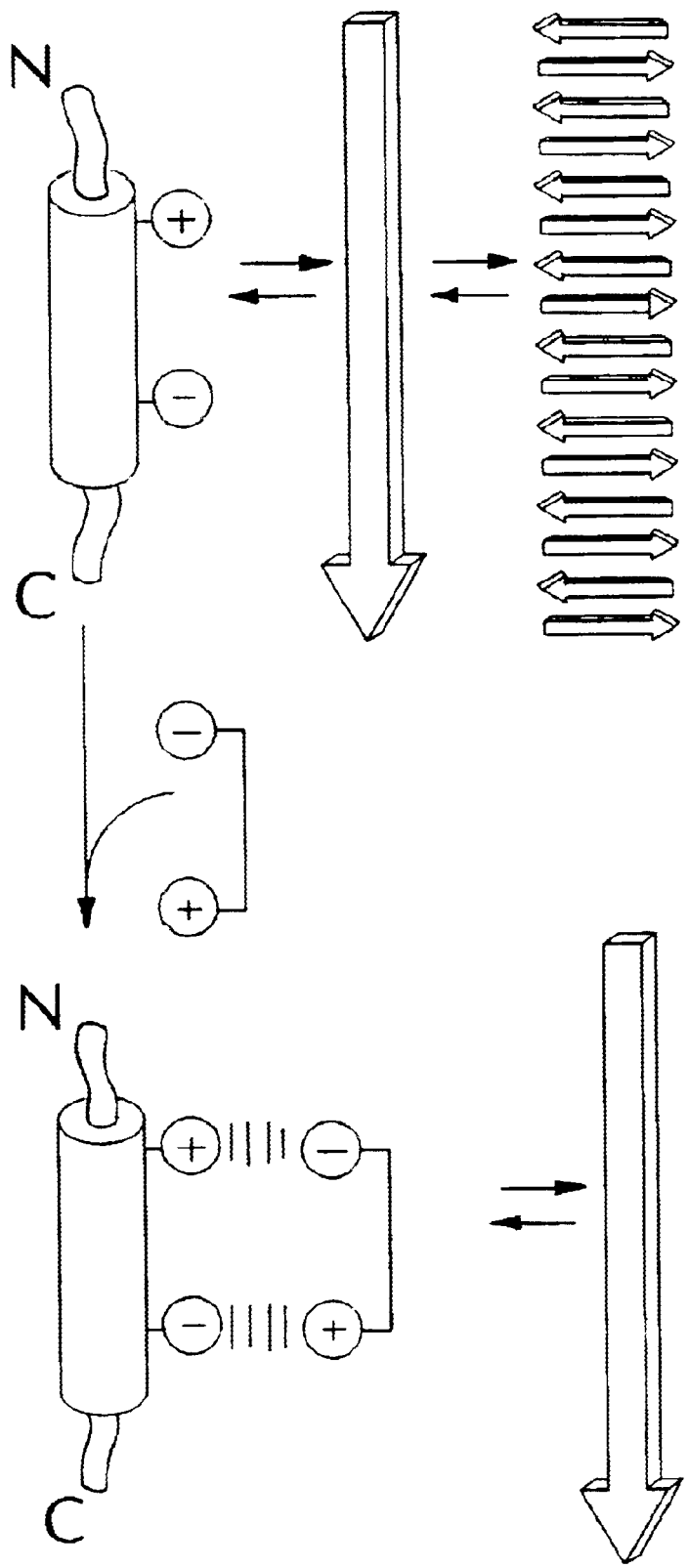
FIG. 12 is a model of Aβ fibril formation and the associated effects of helix-stabilizing agents. The upper row depicts the transformations that helical Aβ peptides are thought to undergo to form β-sheet fibrils. Monomeric Aβ in aqueous solution is structurally disordered (i.e. it interconverts between different structures including α-helical and β-strand conformations) and Aβ in extended conformation will be able to polymerize via the formation of intermolecular contacts in β-sheets. Compounds that can interact preferentially with helical Aβ (here represented by the doubly charged ligand) will shift the equilibrium from the extended conformation and thereby reduce formation of fibrils. The cylinder represents the helix centered around residues 16–23 of Aβ and the + and – signs represent Lys16 and Glu22/Asp23, respectively.

The "helix-lock" mechanism for KAD-induced stabilization of Aβ presented in FIG. 12 is suggested by the following: the match between the KAD tripeptide charged groups and the charges in helical Aβ(15–23); the lack thereof in the other tripeptides and tetrapeptides described in the Examples; the lack of apparent possibilities for KAD to interact with extended Aβ in a more favorable way than the other tripeptides and tetrapeptides; and the observation that the effects of KAD were detected against Aβ(1–40) and Aβ(14–23). In this model, KAD interacts with the charged Lys16 and Glu22/Asp23 in helical Aβ, and thereby stabilizes this conformation relative to extended Aβ. The concomitant shift of the equilibrium towards α-helical Aβ relative to extended Aβ will lower the concentration of an Aβ form that can form β-sheet fibrils. This is expected to result in reduced fibril formation and aggregation of Aβ, as observed experimentally in Examples 4–6. The effects of KAD and acetyl-KAD-amide on fibril morphology (FIG. 9) may also be related to the reduction of fibrillogenic forms of Aβ with concomitant reduced capacity to polymerize.

Stabilization of Discordant Helices as a Means to Prevent Fibril Formation

The results presented in the Examples and the model proposed herein further characterize the relationship between Aβ helix forming potential and the capacity to form fibrils. According to the model, peptide inhibitors (FIG. 12) work at an early step in the fibrilization process by stabilizing helical Aβ and thereby reducing the amount of extended/non-helical peptide that can take part in the polymerization process. The results presented in the Examples suggest that stabilization of helical Aβ can prevent fibril formation and, furthermore, limit the possible interacting residues to the 14–23 region. The latter is intriguing in light of the findings that Aβ(16–23) exhibits α-helix/β-sheet discordance, in common with helix 2 of the PrP and specific helices of at least four additional proteins that can form amyloid fibrils under physiological-like conditions. Mutating Lys16, Leu17 and Phe20 to Ala changes the secondary structure propensity of Aβ(1–28) and stabilizes the Aβ(16–23) helix (i.e. the discordant nature is abolished and instead a helical structure is predicted) and prevents fibril formation. According to the model proposed here (see FIG. 12), KAD can reduce fibril formation by externally stabilizing the discordant Aβ(16–23) helix. It is possible that the discordant helices are stabilized by external factors in their native molecules, e.g., surrounding residues in the three-dimensional structures of globular proteins like PrP, and surrounding lipids in the case of membrane-spanning helices like in Aβ/APP and surfactant protein C.

Pharmaceutical Compositions

The candidate compounds of the invention, i.e., compounds that stabilize the α-helical conformation of a polypeptide containing a discordant helix, can be incorporated into pharmaceutical compositions. Such compositions typically include the candidate compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral (e.g., intravenous, intradermal, subcutaneous), oral, intranasal (e.g., inhalation), transdermal, transmucosal, intrathecal, intracerebral ventricular (e.g., using an Omaya reservoir-shunt with in-line filter that is surgically placed into the cisternal space), and rectal administration. Potentially useful parenteral delivery systems for a composition include slow-dissolving polymer particles, implantable infusion systems, and liposomes. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Treatment of an amylodosis may also be effected by direct delivery of a helix-lock compound to the central nervous system, preferentially to the brain.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating on particles of the active substance (e.g., lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Example of such agents include sugars, polyalcohols such as mannitol and sorbitol, and sodium chloride. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells specifically affected by an amyloidosis with monoclonal antibodies) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of active compound calculated to produce the desired therapeutic effect in association with the required pharmaceutical carrier.

Toxicity and therapeutic efficacy of compounds that stabilize the α-helical form of a discordant helix-containing polypeptide can be determined by standard pharmaceutical procedures in cell cultures or experimental animals, e.g., for determining the LD50 (the dose lethal to 50% of the population) and the ED50 (the dose therapeutically effective in 50% of the population). Suitable animal models can be used such as those described for amyloidoses in Sturchler-Pierrat et al. (1999, Rev. Neurosci., 10:15–24), Seabrook et al.(1999, Neuropharmacol. 38:1–17), DeArmond et al. (1995, Brain Pathology 5:77–89), Telling (2000, Neuropathol. Appl. Neurobiol. 26:209–220), and Price et al. (1998, Science 282:1079–1083). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to unaffected cells and thereby reduce side effects.

Data obtained from the cell culture assays and animal studies can be used in formulating a range of dosage for use in humans. The dosage of a compound lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays in which, e.g., the rate of fibril formation or the rate of cell death is observed. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound of the invention (i.e., an effective dosage) ranges from about 0.001 to 30 mg/kg body weight, preferably about 0.01 to 25 mg/kg body weight, more preferably about 0.05 to 20 mg/kg body weight, and even more preferably about 0.1 to 10 mg/kg body weight. The compound can be administered over an extended period of time to the subject, e.g., over the subject's lifetime. In some cases the compound can be administered one time per week for between about 1 to 10 weeks, preferably between 2 to 8 weeks, more preferably between about 3 to 7 weeks, and even more preferably for about 4, 5, or 6 weeks. The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

For compounds that are antibodies, the effective dosage may range from about 0.0001 to at least 100 mg/kg body weight. An antibody dosage can be 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration may be possible with a humanized antibody. Modifications such as lipidation can be used to stabilize antibodies and to enhance uptake and tissue penetration (e.g., into the brain). A method for lipidation of antibodies is described by Cruikshank et al. (1997, J. Acquired Immune Deficiency Syndromes Hum. Retrovirol. 14:193).

A compound for example, may be a small molecule. Such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole. Such compounds can also be organic or inorganic compounds having a molecular weight less than about 5,000 grams per mole, organic or inorganic compounds having a molecular weight less than about 1,000 grams per mole, or organic or inorganic compounds having a molecular weight less than about 500 grams per mole. The compounds can be in any pharmaceutically acceptable form such as a salt or ester. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to treat a disease in which a discordant helix-containing protein is involved (e.g., an amyloidosis), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Compounds that can be used in pharmaceutical compositions include tripeptides and tetrapeptides such as those described in the Examples, e.g., peptides having the sequence KAD or KFD. The peptides of the pharmaceutical compositions can be dipolar, neutral, or mono-charged. By "dipolar peptide" is meant a peptide having a positively charged amino acid (e.g., K, R, or H) at one terminus and a negatively charged amino acid (e.g., D or E) at the other terminus. The charge of an amino acid residue refers to its charge as imparted by its side chain, not to the charge resulting from a free amino or carboxy terminus. In addition to the peptides KAD and KFD, other examples of dipolar tripeptides include DAK, DFK, RAD, RFD, DAR, DFR, KAE, KFE, EAK, EFK, RAE, RFE, EAR, EFR, or any of the above with the middle residue substituted by another uncharged residue such as G, I, L, S, T, W, Y, or V. The peptides can have protected termini. Also useful are peptide mimetics that mimic the structure of such peptides, but lack peptide bonds.

The pharmaceutical compositions of the invention can be included in a container, pack, or dispenser together with instructions for administration. For example, the instructions can include directions to use the composition to treat an individual having or at risk for an amyloidosis.

Methods of Treatment

The present invention provides for both prophylactic and therapeutic methods of treating a subject at risk of (or susceptible to) a disorder or having a disorder associated with fibril formation such as an amyloidosis. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, and antibodies.

In one aspect, the invention provides a method for preventing a disease or condition (i.e., decreasing the risk of contracting, or decreasing the rate at which symptoms appear that are associated with a disease or condition) associated with fibril formation caused by a polypeptide containing a discordant helix, by administering to the subject a compound that stabilizes the α-helical form of the polypeptide. Subjects at risk for a disease (e.g., an amyloidosis) that is caused or exacerbated by such polypeptides can be identified by, for example, any or a combination of appropriate diagnostic or prognostic assays known in the art. Administration of a prophylactic agent can occur prior to the manifestation of symptoms characteristic of the disease, such that the disease is prevented or, alternatively, delayed in its progression.

In instances where a target antigen (e.g., discordant helix) is intracellular and whole antibodies are used to treat the subject, internalizing antibodies may be preferred. Lipofectin or liposomes can be used to deliver the antibody or a fragment of the $F_{ab}$ region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., 1993, Proc. Natl. Acad. Sci. USA 90:7889–7893).

The compounds that stabilize the α-helical form of a discordant helix-containing polypeptide can be administered to a patient at therapeutically effective doses to prevent, treat or ameliorate disorders involving fibrin. formation (e.g., amyloidoses). A therapeutically effective dose refers to that amount of the compound sufficient to result in amelioration of symptoms of the disorders. Toxicity and therapeutic efficacy of such compounds can be determined by standard pharmaceutical procedures as described above.

The invention will be further described in the following examples, which do not limit the scope of the invention described in the claims.

EXAMPLES

To test the hypothesis that α-helices for which β-strand structures are predicted are prone to undergo a transition from α-helix conformation to β-strand conformation and amyloid formation, we searched for conflicts between α-helices that were previously determined and predicted extended structures in 1324 non-redundant entries in a protein data bank. The data demonstrate a correlation between the presence of a discordant helix in a polypeptide and the ability of the polypeptide to form amyloid fibrils under physiological conditions.

Example 1

Identification of α-Helical Protein Segments that are Predicted to Form β-Strands The occurrence of α-helices that have a high statistical likelihood of being in β-strand conformation was analyzed by submitting a non-redundant set of protein sequences with known three-dimensional structures (1324 proteins; a total of 269,058 amino acid residues) to the neural network program PHD for secondary structure prediction.

Protein Data Set

A non-homologous set of proteins used for this study was generated using the May 1999 list of PBD_SELECT (Hobohm et al., 1992, Protein Sc., 1:409–417; Hobohm et al., 1994, Protein Sci., 3:522–524) from the Brookhaven database (Berman et al., 2000, Nucleic Acids Res. 28:235–242). This list consisted of 1106 chain identifiers, where all proteins have less than 25% residue identity in pairwise comparisons. A new version of PBD_SELECT was released in November of 1999 (November set). Proteins from the November set that were non-overlapping with the May set were added to the data set used in the studies described herein. The comparisons between the two releases to determine which proteins were non-overlapping were made using FASTA (Pearson et al., 1998, Proc. Natl. Acad. Sci. USA, 85:2444–2448). Proteins in the November set that had an expected value higher than 0.1 compared to any of the proteins in the May set were added to the May set to produce the complete set of proteins studied as described herein. A total of 218 non-overlapping proteins from the November set were added to the to the May data set. The resulting data set of protein structures investigated thus consisted of 1324 non-homologous proteins.

Experimentally Determined Secondary Structures

Secondary structure elements of selected proteins were extracted from the PBD files by DSSP (Define Secondary Structure of Proteins; Kabsch et al., 1983, Biopolymers, 22:2577–2637), as implemented in ICM (Abagyan et al., 1994, J. Mol. Biol. 235:983–1002). This method defines secondary structure elements from hydrogen bond patterns. The method distinguishes eight different classes of structure: α-helix (H); $3_{10}$-helix (G); Π-helix (I); extended strand (E); isolated β bridge (B); turn (T); bend (S), and coil (-). Herein three classes of secondary structures are being considered: helix (H, G and I); strand (E); and loop (B, T, S and -), since these three classes are employed by the method used for secondary structure prediction. These experimentally determined structures were compared with the predicted secondary structures generated by PHD, described below.

Predicted Secondary Structures

The sequence-specific secondary structures for the proteins in the data set were predicted using PHD (Profile network from HeiDelberg; Rost et al., 1993, J. Mol. Biol. 232:584–599; Rost et al., 1994, Proteins 19:55–77). PHD employs a system of neural networks and has an overall accuracy of about 72%.

Chou and Fasman (1978, Adv. Enzymol. 47:45–148) used the sequences of 29 proteins to calculate the amino acid distributions in helices, Pα, and beta strands, Pβ. The P values are calculated as the frequency of each amino acid residue in α-helix (or β-strand) regions divided by the average frequency of all residues in α-helix (or β-strand) regions. For the study herein, the Chou and Fasman values were recalculated using the PDB May data set described above. Chains that correspond to transmembrane proteins were removed from the data set, resulting in a set of 1091 proteins. Stretches of a least five consecutive residues of helix (H) or beta strand (E), were included in the calculations. The resulting Pα and Pβ values are provided in Table 1. Table 1 shows the calculated propensities of each of the twenty amino acids to occur in an α-helix or in a β-strand. These calculations were based on available protein three-dimensional structures in the protein databank (PDB), derived as described herein. The values in Table 1 were used to predict the secondary structures of different protein segments (see FIGS. 2, 4, and 5) as described below. The Chou and Fasman values confirm the results of the database search done using PHD (see FIG. 1, infra).

TABLE 1

Propensity values for α-helices (Pα) and n-strands (Pβ) calculated according to the method of Chou and Fasman (Chou et al., 1978, Adv. Enzymol., 47:45–148) from a set of 1091 non-redundant proteins. The Pα and Pβ values derived originally from a set of 29 proteins are given in parentheses. P values that differ > 0.15 between the two data sets are in boldface type.

| Amino Acid | Pα | Pβ |
|---|---|---|
| A | 1.46 (1.42) | 0.78 (0.83) |
| C | 0.75 (0.70) | 1.26 (1.19) |
| D | 0.83 (1.01) | 0.51 (0.54) |
| E | 1.37 (1.51) | 0.69 (0.37) |
| F | 0.97 (1.13) | 1.49 (1.38) |
| G | 0.43 (0.57) | 0.69 (0.75) |
| H | 0.90 (1.00) | 1.05 (0.87) |
| I | 1.07 (1.08) | 1.65 (1.60) |
| K | 1.14 (1.16) | 0.78 (0.74) |
| L | 1.36 (1.21) | 1.13 (1.30) |
| M | 1.25 (1.45) | 1.10 (1.05) |
| N | 0.72 (0.67) | 0.64 (0.89) |
| P | 0.40 (0.57) | 0.32 (0.55) |
| Q | 1.34 (1.11) | 0.82 (1.10) |
| R | 1.24 (0.98) | 0.88 (0.93) |
| S | 0.76 (0.77) | 0.88 (0.75) |
| T | 0.76 (0.83) | 1.21 (1.19) |
| V | 0.94 (1.06) | 1.89 (1.70) |
| W | 1.05 (1.08) | 1.39 (1.37) |
| Y | 0.95 (0.69) | 1.47 (1.47) |

Comparison of Experimentally Determined and Predicted Data Sets

The occurrence of α-helices that have high statistical likelihood of being in β-strand conformation was analyzed by submitting the experimentally determined data set whose proteins have known three-dimensional structures to the neural network program PHD for secondary structure prediction, generating a predicted data set.

Comparison of the experimentally determined and predicted data sets revealed 37 proteins containing 7-residue or longer α-helices that were predicted (PHD reliability index >5) to be in β-strand conformation (FIG. 1). This condition is referred to as α-helix/β-strand discordance and such helices are discordant helices. The number of discordant stretches increases steeply for segments containing at 6-residues or less (FIG. 1).

Figure 2A:
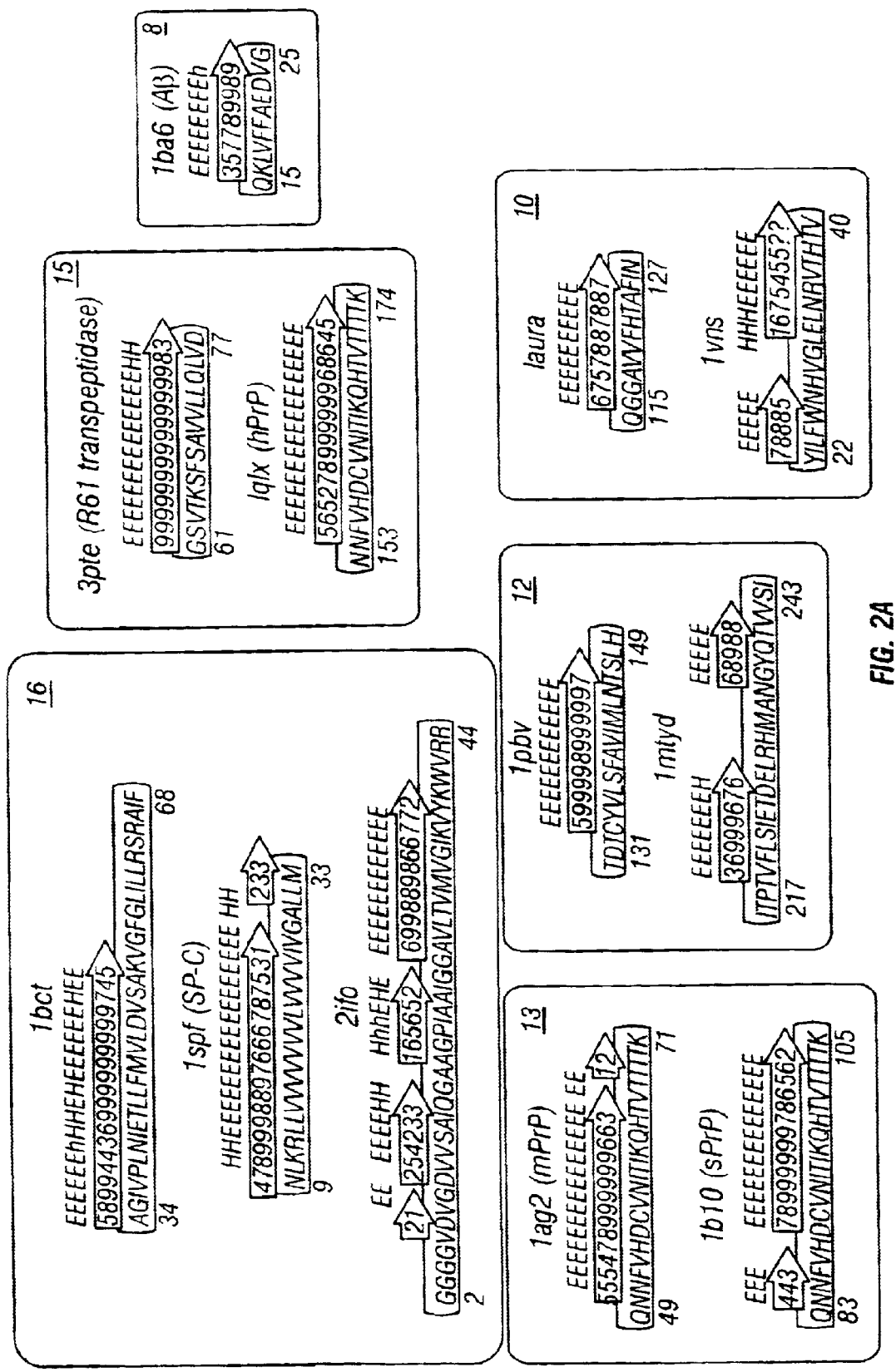
FIGS. 2A–2B are a set of diagrams that depict the characteristics of long discordant helix segments. Amino acid sequences, together with determined and predicted secondary structure elements for sequences having ≧9=residue discordant segments are shown. Also shown are those discordant segments of Aβ, mouse PrP, and human PrP. The proteins are grouped by the length of their discordant stretch. The experimentally determined helical segments are drawn as blue cylinders in the bottom row of each case in which the amino acid sequences and residue positions in the PDB entries of the corresponding proteins are given (Top to bottom in each set: Set 16 contains SEQ ID NOs:4–6; Set 15 contains SEQ ID NOs:7 and 8; Set 8 contains SEQ ID NO;9; Set 13 contains SEQ ID NOs:10 and 11; Set 12 contains SEQ ID NOs:12 and 13; Set 10 contains SEQ ID NOs:14 and 15; Set 11 contains SEQ ID NOs:16–18; Set 9 contains SEQ ID NOs: 19–20 (top row left to right) and 21–23 (bottom row left to right). The locations of the β-strands predicted by PHD are visualized by yellow strands in the middle row of each case, wherein the reliability index for each residue is shown. The Chou-Fasman-based predictions averaged for 6-residue segments are plotted above residue 3 in each segment and given in the top row of each case. E and e denote extended structures (i.e., β-strands) predicted with high and low probability, respectively, as in Chou and Fasman (1978, Adv. Enzymol. 47:45–148), and H and h represent predicted helical structures in an analogous manner.
Figure 2B:
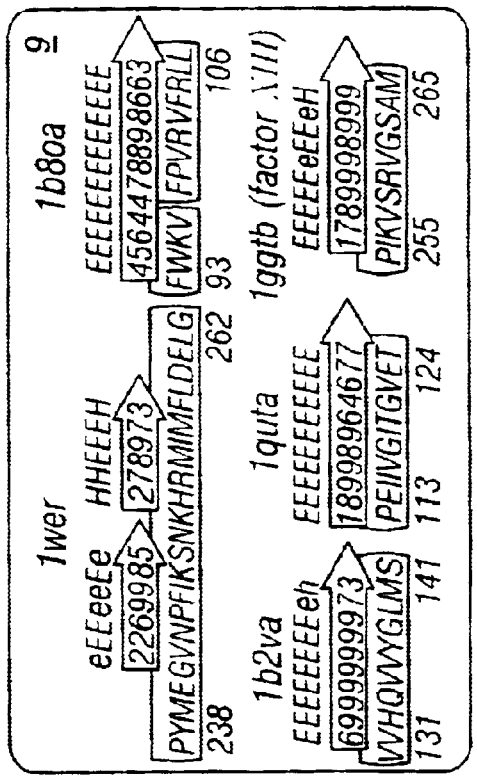
Figure 2B:
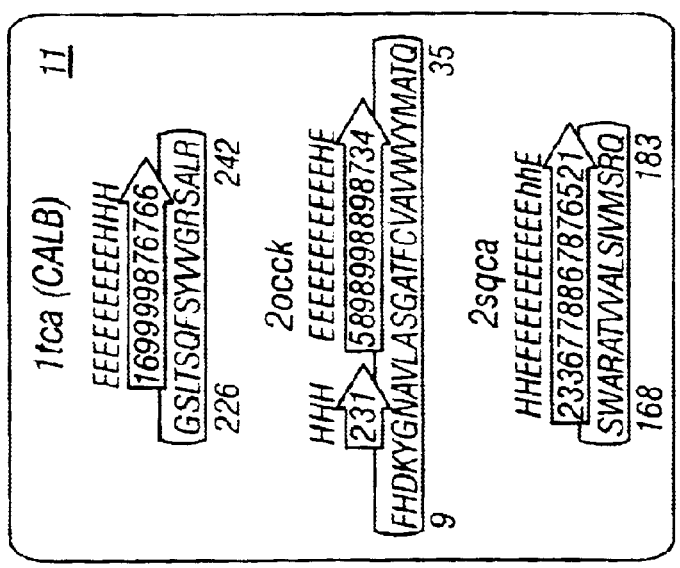
Figure 3:
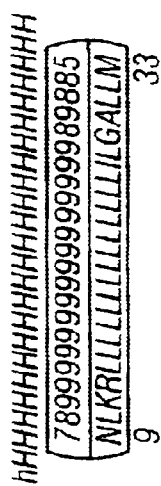
FIG. 3 is a diagram that depicts the amino acid sequence (bottom row; SEQ ID NO:24) and predicted secondary structure by PHD and according to Chou-Fasman analysis for a polyleucine analogue of SP-C (lung surfactant protein C). The PHD predictions including reliability indices are given in the middle row and the Chou-Fasman data in the top row, but in this case an α-helix is predicted by both methods, symbolized by a blue cylinder for the PHD prediction.

Secondary structure predictions based on α-helix and β-strand propensity values that were calculated according to the Chou-Fasman methods (Chou et al., 1978, Adv. Enzymol. 47:45–148; Table 1) produced results in agreement with the PHD results, confirming the α-helix/β-strand discordant nature of the identified segments (FIG. 2). Only proteins with >7-residue discordant helices were subjected to additional analysis. FIG. 2 illustrates the amino acid sequences as well as experimentally determined and predicted secondary structures for the 17 proteins with >9-residue discordant segments. The 8-residue discordant segment of the Aβ peptide and the discordant segments of all three prion proteins for which NMR structures were determined (Zahn et al., Proc. Natl. Acad. Sci. USA, 97:145–150, 2000; Riek et al., Nature, 382: 180–182, 1996; James et al., Proc. Natl. Acad. Sci. USA, 94:10086–10091, 1997) are also included in FIG. 2, because of their importance in amyloidoses.

The proteins identified as containing α/β discordant segments represent a wide variety of structures (ranging from single helical peptides to large globular proteins with complex α/β architectures), localizations (nuclear, cytosolic, integral and peripheral membrane proteins, as well as extracellular proteins), and species of origin (ranging from virus to human). The proteins encompass three proteins known to be amyloidogenic in vivo, i.e., the prion protein (PrP, 12- or 15-residue discordant segment, depending on species, in helix 2), the Aβ peptide (8-residue segment), and SP-C (16-residue segment) (FIGS. 1 and 2). No consensus pattern in the primary structures of the α-helix/β-strand discordant segments could be detected. A proposed consensus sequence for amyloid-forming proteins was not found (Kurochkin, 1998, FEBS Letters 427:153–156), nor was a binary pattern of hydrophobic and hydrophilic residues found in the fibrillating peptides (West et al., 1999, Proc. Natl. Sci. USA 96:11211–11216).

Among the proteins with >7-residue discordant segments, four are integral membrane proteins or parts thereof (bacteriorhodopsin, cytochrome c oxidase, SP-C, Aβ). The driving forces for α-helix formation in a membrane environment differ from those in aqueous solution (Li et al., 1994, Nat. Struct. Biol. 1:368–373) and the secondary structure prediction methods used herein were based mainly on structural data from soluble proteins. However, both Aβ and SP-C form amyloid in vivo. Although the proteins identified as containing discordant helices encompass a broad range of functions, many are enzymes (23/37 proteins) or other proteins that bind ligands (FIGS. 1 and 2).

A discordant helix of the invention can harbor an active site residue or ligand-interacting residue. For example, the metalloproteases astacin (1iab) and adarnalysin II (3aig), and methane monoxygenase (1mty) harbor zinc- or iron-binding residues in their respective discordant helix (Bode et al., 1992, Nature 358:164–167; Gomis-Ruth et al., 1998, Protein Sci. 7:283–289; Rosenzweig et al., 1995, Chem.

Biol. 2:409–418). The discordant helix of heme-binding protein A (1B2v) contains several residues important for heme binding (Arnoux et al., 1999, Nat. Struct. Biol. 6:516–520). In the Arf exchange factor ARNO (1pbv), the discordant helix is involved in Arf binding (Cherfils et al., 1998, Nature 392:101–105); the discordant helix of the light-driven ion pump bacteriorhodopsin (1bcr) binds the photo-sensitive retinal (Barsukov et al., 1992, Eur. J. Biochem. 206:665–672, 1992). The active-site serine of Streptomyces R61 transpeptidase is located in the discordant helix (Kelly et al., 1985, J. Biol. Chem. 260:6449–6458).

Example 2
Protein Analysis and Electron Microscopy of Proteins with Long Discordant Helices Formation of fibrils was investigated in three different proteins having long discordant helices by incubating proteins, centrifuging, and examining the pellets for fibrils using electron microscopy. In addition, the effect on fibril formation of a valine to leucine substitution in a discordant helix of a fourth protein (SP-C) was investigated.

The proteins used in these experiments included SP-C (lung SP-C forms amyloid in pulmonary alveolar proteinosis) purified from porcine lungs (Curstedt et al, 1987, Eur. J. Biochem. 168:255–262). PolyVal→polyLeu substituted SP-C (SP-C(Leu)) analogue was synthesized as described by Nilsson et al. (1998, Eur. J. Biochem, 255:116–124) was used in the experiments as was D-analyl-D-alanine transpeptidase from Streptomyces R61 was obtained from Drs. Frere and Joris, University of Liege, Belgium (Frere et al, 1973, Biochem. J. 135:463–468). Triacylglycerol lipase from *Candida antarctica* and human coagulation factor XIII were purchased from Sigma. For these fibrillation studies the latter three proteins were dissolved in phosphate buffered saline, pH 7.4, in concentrations ranging from 10 $\mu$M to 100 $\mu$M. SP-C and SP-C (Leu) were dissolved at 100 $\mu$M or 250 $\mu$M in chloroform/methanol/0.1 M HCl, 32:64:5 (by volume).

To assay for the formation of fibrils, the protein solutions were incubated at 37° C. for three days, then centrifuged at 20,000× g for 20 minutes. The concentrations of SP-C and SP-C(Leu) in the supernatants were determined by amino acid analysis of triplicate samples. Peptide concentration at start of the incubations was 250 $\mu$M for SP-C(Leu) and 100 $\mu$M for SP-C.

For analysis of fibrils by electron microscopy, the 20,000× g pellets were resuspended in a small volume of water using low-energy sonication for 5 seconds. Aliquots of 8 $\mu$l were placed on grids covered by a carbon-stabilized Formvar® film. Excess fluid was withdrawn after 30 seconds. The grids were air-dried and negatively stained with 2% uranyl acetate in water. The strained grids were examined and photographed in a Philips CM120-TWIN electron microscope operated at 80 kV.

D-analyl-D-alanine transpeptidase, triacylglycerol lipase, and coagulation factor XIII were all found to form fibrils under the experimental conditions. In the case of SP-C, fibrils were readily detected in the 20,000× g pellets within a few hours of incubation (Gustafson et al., 1999, FEBS Lett. 464:138–142), while for SP-C(Leu) no or very few fibrils were found after three days of incubation.

These data demonstrate that the presence of a discordant helix can predict formation of fibrils, reflecting the ability of these proteins to form β-strand structures that can contribute to amyloid formation. Furthermore, the dramatic reduction in the number of fibrils formed by SP-C(Leu) shows that alteration of the discordant helix can prevent or slow fibril formation.

Example 3
α/β Discordant Segments Predispose to Amyloid Fibril Formation.

Three proteins known to be amyloidogenic and associated with disease were found among the α/β discordant proteins. The fibril formation properties of additional proteins containing predicted discordant helices were investigated.

As described above, transpeptidase from Streptomyces R61 (15-residue discordant stretch), triacylglycerol lipase from *Candida antarctica* (11-residue stretch), and human coagulation factor XIII (9-residue segment) were found to form amyloid fibrils upon incubation for 3 days in phosphate buffered saline at pH 7.4 at 37° C. Thus, 6/37 proteins with ≧7-residue long α/β discordant segments, and 4/10 with segments of ≧11 residues, were analyzed for fibril formation. All form amyloid fibrils.

Figure 4:
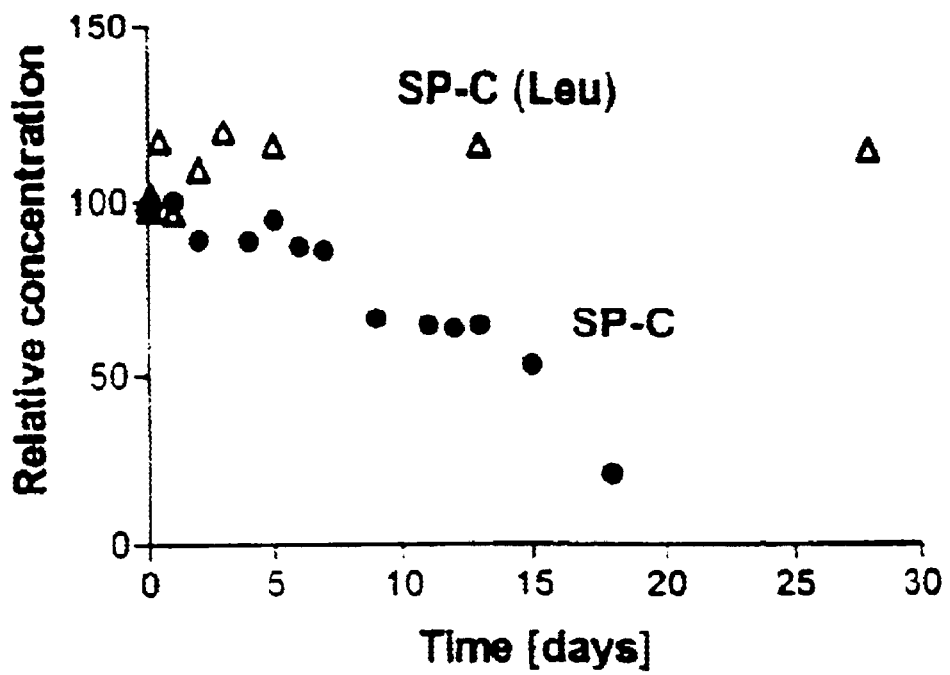
FIG. 4 is a graph that depicts data from an experiment in which the relative amounts of SP-C(squares) and SP-C(Leu) (triangles) remaining in solution after centrifugation at 20,000× g for 20 minutes at different time points after solubilization were measured.

The correlation between α/β discordance and fibril formation suggests a causal connection between these two phenomena. We thus predicted that changes in amino acid sequences that abolish α/β discordance would reduce amyloid formation. Two approaches were used to test this. First, all of the valine residues in the α-helix/β-strand discordant segment of SP-C were replaced with leucine, yielding a peptide, SP-C(Leu), with helical conformation as judged by circular dichroism and infrared spectroscopy (Nilsson et al, 1998, Eur. J. Biochem. 255:116–124). Val to Leu substitutions in SP-C abolish α/β discordance and reduce amyloid formation (FIG. 4). FIG. 2 depicts the sequence of native SP-C and its predicted secondary structure. The localization of the α-helix of SP-C(Leu) is inferred from the NMR data of the native peptide (Johansson et al., 1994, Biochemistry 33:6015–6023) and CD and FTIR spectroscopic analyses of the analogue (Nilsson et al, 1998, Eur. J. Biochem. 255:116–124).

The time-dependent aggregation of SP-C and SP-C(Leu) showed striking differences (FIG. 4). SP-C started to precipitate during the first hours of incubation and showed extensive aggregation after 5 and 15 days. SP-C(Leu) showed no signs of precipitation during the same time period. The leucine-substituted analogue formed few fibrils after incubation for three days at 250 $\mu$M concentration, while SP-C formed abundant fibrils at a concentration of 100 $\mu$M. Thus, fibril formation and peptide aggregation is greatly reduced by converting the discordant helix of SP-C to a helix composed of residues that favor the helical conformation.

Figure 5:
FIG. 5 is a set of diagrams that depict the experimentally determined and predicted secondary structures of positions 1–28 of Aβ (SEQ ID NO:25; top) and a valiant of Aβ (1–28) in which three residues have been changed to alanine (K16A, L17A, F20A) (SEQ ID NO:26; bottom). Symbols are as described for FIGS. 2 and 4.

In a second approach, a synthetic analogue of the Aβ peptide that lacks residues 14–23, and thus is devoid of the α/β discordant stretch between residues 16 and 23 (FIG. 2) but otherwise identical to human Aβ(1–42) was incubated under conditions where Aβ(1–42) readily forms fibrils (Tjernberg et al., 1999, J. Biol. Chem. 274:12619–12625). The synthetic analogue did not form fibrils. Moreover, Aβ(1–28) with alanine substitutions at positions 16, 17, and 20 does not form fibrils, while unsubstituted Aβ(1–28) forms fibrils which are similar to those formed by Aβ(1–42) (Tjernberg et al., 1996, J. Biol. Chem., 271:8545–8548). We discovered that substitution of alanine into positions 16, 17, and 20 reverts α/β discordance and a helix is predicted between residues 15 and 21 (FIG. 5). Thus, when discordant helix is removed from an Aβ peptide, or rendered nondiscordant by replacement of three residues, the peptide no longer forms fibrils.

These data support a causal link between the presence of a discordant helix in a protein and fibril formation that is expected to lead to the formation of amyloid.

Example 4
Effects of Peptides on Aβ(1–40), Aβ(12–24) and Aβ(14–23) Fibril Formation The 39–43 amino acid residue amyloid β-peptide (Aβ) is present in amyloid plaques found in association with Alzheimer's disease (Selkoe, 2000, J. American Medical Association 283:1615–1617). In addition, the amount of Aβ(1–42) in Alzheimer's disease plaques correlates with disease progression, implying that Aβ is a rational therapeutic target (Näslund et al., 2000, J. American Medical Association 283:1571–1577). Aβ is generated by proteolytic cleavage of a large transmembrane protein, the amyloid precursor protein (APP). The present studies evaluate various peptides for their ability to inhibit the fibril formation by Aβ peptides.

Synthetic peptides corresponding to human Aβ fragments 1–40 (amino acid sequence DAEFRHDSGYEVH-HQKLVFFAEDVGSNKGAIIGLMVGGVV; SEQ ID NO:3), 12–24, and 14–23 were purchased from Research Genetics, Huntsville, Ala., USA. Aβ(1–40) was purified by reverse-phase HPLC over a C18 column, using a linear gradient of acetonitrile running into 0.1% trifluoroacetic acid for elution. The purified peptide was lyophilized, stored at −20° C. and dissolved shortly before experiments. The tripeptides and tetrapeptides were synthesized and purified by reverse-phase HPLC (>70% purity) by Interactive, Darmstadt, Germany.

The relative abundance and morphology of fibrils was determined by electron microscopy after incubating each of the three Aβ peptides (100 μM) for three days at 37° C. in phosphate buffered saline (50 mM sodium phosphate/50 mM NaCl, pH 7.4) in the presence of 1 mM of a specific tripeptide or tetrapeptide ligand. Aggregates were collected by centrifugation at 20,000× g for 20 minutes. The pellets were suspended in a small volume of water by low-energy sonication for 5 seconds. Aliquots of 8 μl were placed on electron microscopy grids covered by a carbon-stabilized formvar film. Excess fluid was withdrawn after 30 seconds, and after air-drying the grids were negatively stained with 2% uranyl acetate in water. The stained grids were examined and photographed in a Philips CM120TWIN electron microscope operated at 80 kV. For a semi quantitative evaluation of the amount of material in the different specimens, the grids (50 mesh) were first scanned at low magnification and the number of larger fibril bundles per grid square estimated. The specimens were subsequently examined at high magnification to judge the size of the fibril bundles, the presence of smaller fibril aggregates, and the morphology of the individual fibrils.

Figure 6A:
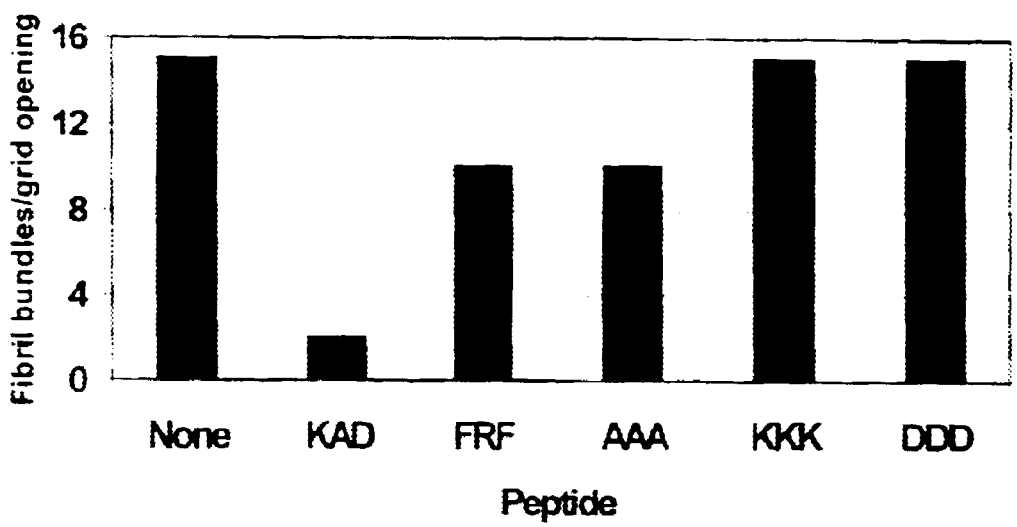
FIGS. 6A–6C are graphs depicting the effects various tripeptides on fibril formation by Aβ(14–23) (FIG. 6A). Aβ(12–24) (FIG. 6B), and Aβ(1–40) (FIG. 6C). Unless otherwise indicated, the tripeptides have free N- and C-termini. The results are representative for two to three independent experiments.
Figure 6B:
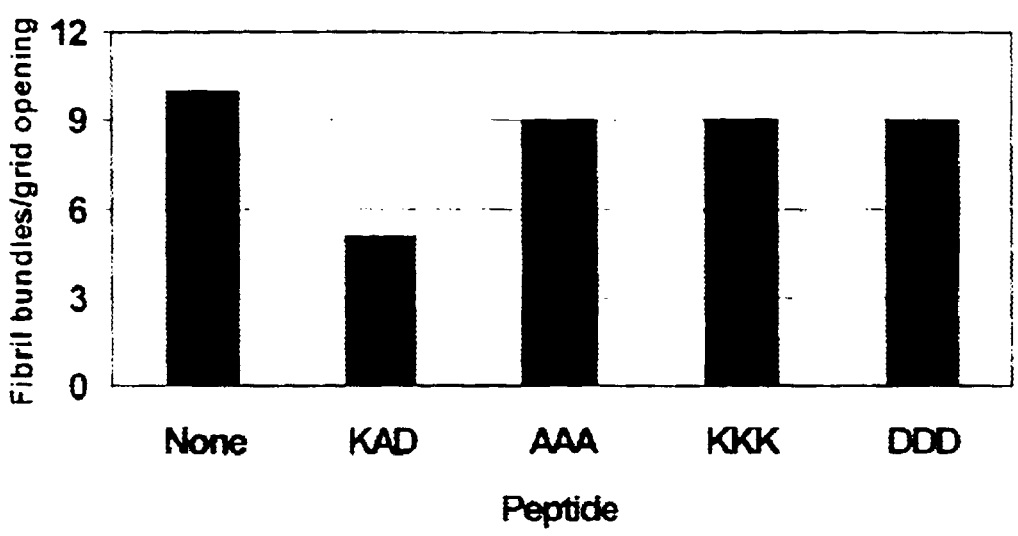
Figure 6C:
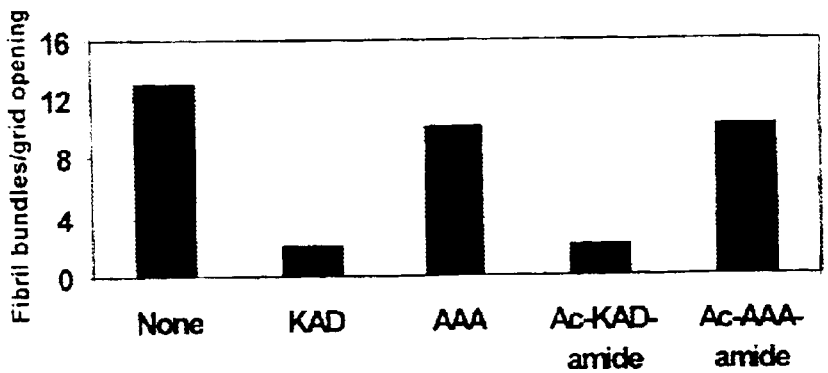

In these experiments, the density of fibrils with a morphology similar to that of fibrils formed from the Aβ peptides in the absence of tripeptides or tetrapeptides was estimated. For all three Aβ peptides, a significant reduction of fibril density was observed in the presence of the KAD tripeptide, but not in the presence of FRF, AAA, KKK, or DDD tripeptides (FIGS. 6A–6C). A KAD peptide with blocked N- and C-termini (acetyl-KAD-amide) was found to be equally efficient in reducing Aβ(1–40) fibril formation as the KAD peptide with free termini (FIG. 6C). Likewise, both AAA and acetyl-AAA-amide showed no significant effect on Aβ(1–40) fibrillation (FIG. 6C). These experiments indicate that a tripeptide with a dipolar character can reduce Aβ fibril formation, and that the region between Aβ residues 14 and 23 is involved in tripeptide/Aβ interactions.

Figure 7:
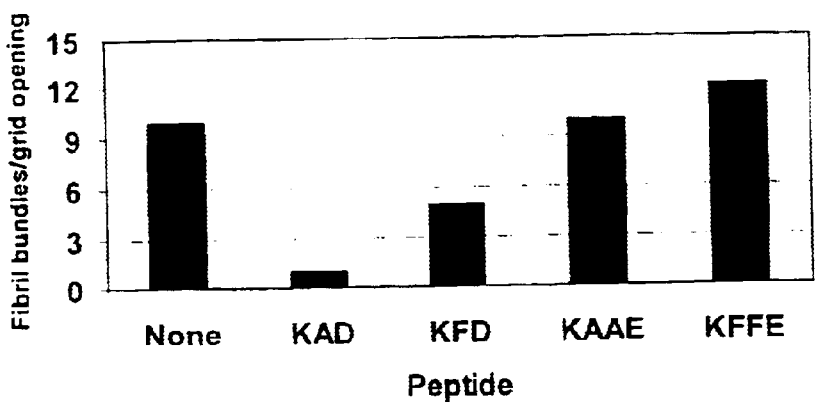
FIG. 7 is a graph depicting the effects of various tripeptides and tetrapeptides on fibril formation by Aβ(14–23).

The importance of the identity of the central amino acid residue of the ligand peptide and of ligand peptide length was also investigated. Replacing the central Ala with Phe resulted in a tripeptide (KFD) that reduced Aβ(14–23) fibril formation, but to a lesser extent than KAD (FIG. 7). Extending the length of the dipolar peptides by one residue resulted in peptides that caused no detectable reduction of Aβ(14–23) fibrillation (FIG. 7). The tetrapeptide KFFE (SEQ ID NO:1) appeared to slightly promote fibril formation (FIG. 7).

Example 5
Effects of Peptides on Aggregation of Aβ(1–40)

Figure 8:
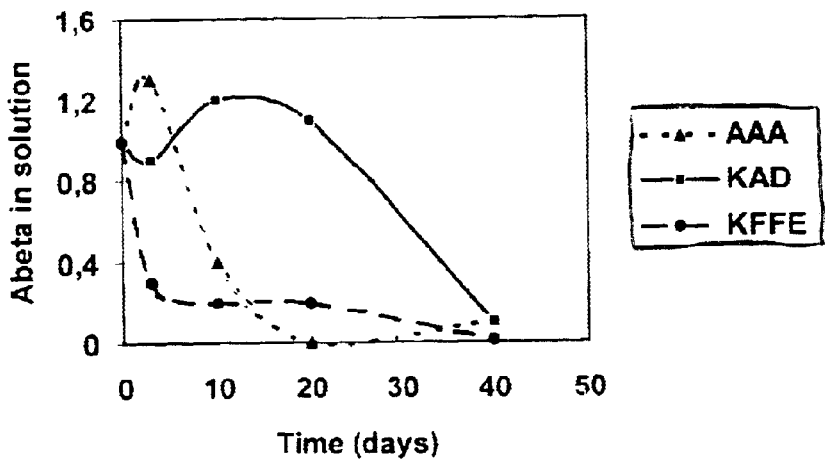
FIG. 8 is a graph depicting the effects of the peptides KAD, AAA, and KFFE (SEQ ID NO:1) on Aβ(1–40) aggregation. Samples were analyzed in duplicate.
Figure 9A:
FIGS. 9A–9E depict the fibrillar structures of Aβ(1–40) formed in the absence of tripeptide (9A), in the presence of KAD (9B), acetyl-KAD-amide (9C), AAA (9D), or acetyl-AAA-amide (9E).
Figure 9B:
Figure 9C:
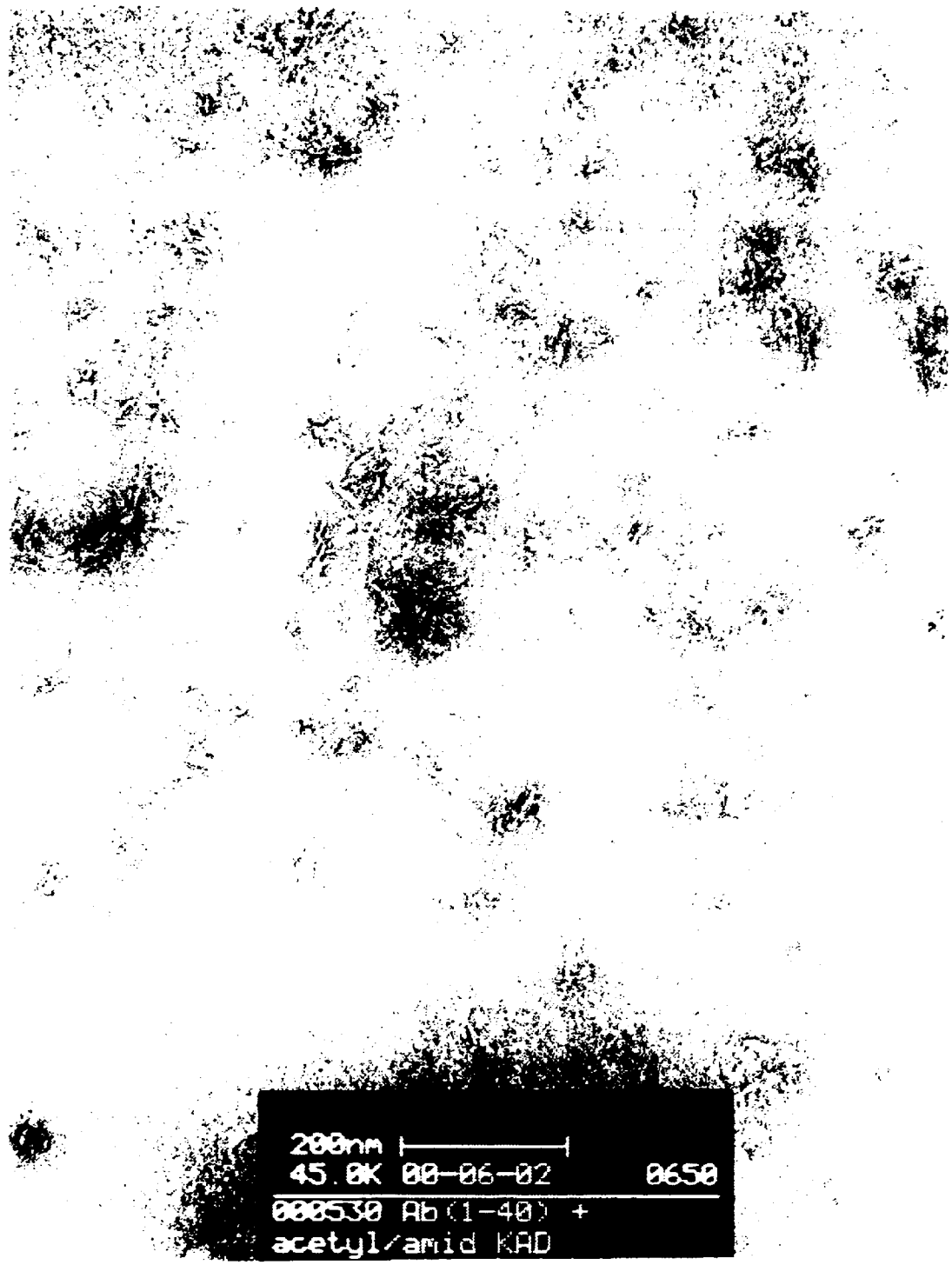
Figure 9D:
Figure 9E:

The effects of the peptides KAD, AAA, and KFFE (SEQ ID NO:1) on the time-dependent aggregation of Aβ(1–40), determined as the amount of Aβ(1–40) left in solution after 20,000× g centrifugation, were studied. In the presence of AAA, Aβ(1–40) completely aggregated in 10–15 days. In the presence of KAD, Aβ(1–40) completely aggregated in 30–40 days. In the presence of KFFE (SEQ ID NO:1), Aβ(1–40) completely aggregated in about 3 days (FIG. 8). These results are in agreement with the results obtained from the fibrillation studies presented in Example 4 regarding the relative efficiency of KAD, AAA and KFFE (SEQ ID NO:1) in reducing Aβ fibrillation (FIGS. 6 and 7).

Example 6
Effects of Peptides on Fibril Morphology

The presence of the KAD peptide resulted in the formation of fibrils with different morphology than those formed in its absence or in the presence of other tripeptides or tetrapeptides. The presence of the KAD, or acetyl-KAD-amide, peptide resulted in fibrillar structures that were much shorter and more dispersed than those formed in the presence of AAA or acetyl-AAA-amide (FIGS. 9A–9E). The presence of other tripeptides or tetrapeptides investigated resulted in very similar fibril morphology as seen with AAA.

Example 7
Structures of Tripeptides and Tetrapeptides and Separation of Charges in Aβ(16–23)

The different effects observed in Example 4–7 for KAD/acetyl-KAD-amide, as compared to AAA/acetyl-AAA-amide, FRF, KKK, and DDD may be the result of the peptides' different charge distributions. These Examples show that the dipolar KAD, but not the neutral or mono-charged tripeptides, interfere with Aβ aggregation and fibril formation. In addition, a reduction of fibril formation is also seen with the dipolar KFD peptide, although to a lesser extent than that observed with KAD.

Figure 10:
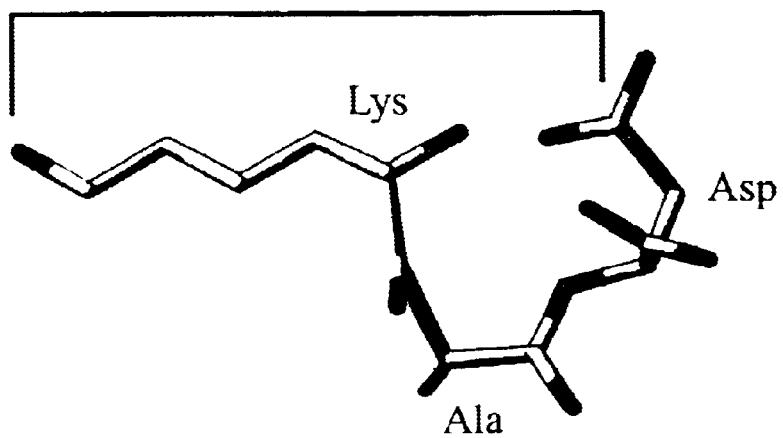
FIG. 10 depicts the KAD peptide in an energy-minimized conformation (top structure), the KAD peptide in an extended conformation (middle structure), and the KFFE (SEQ ID NO:1) peptide in an extended conformation (bottom structure). The amino and carboxyl groups of the charged side-chains are on the same side of the polypeptide backbone in KAD and the distances between them are then shown. In KFFE, the charged side-chains are on opposite sides of the polypeptide backbone.
Figure 10:
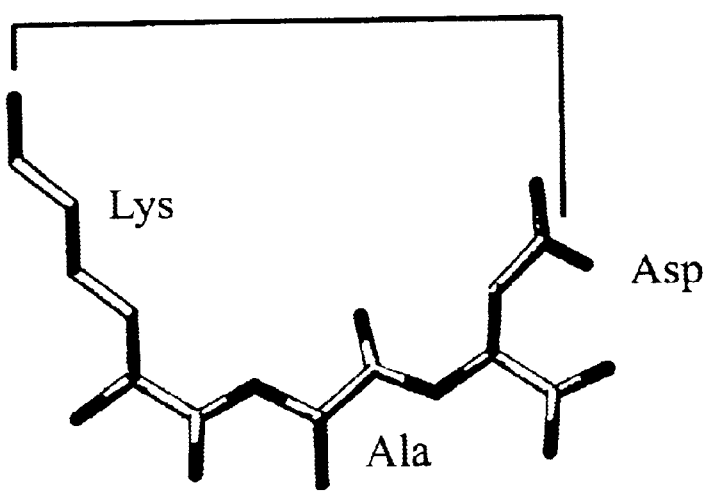
Figure 10:
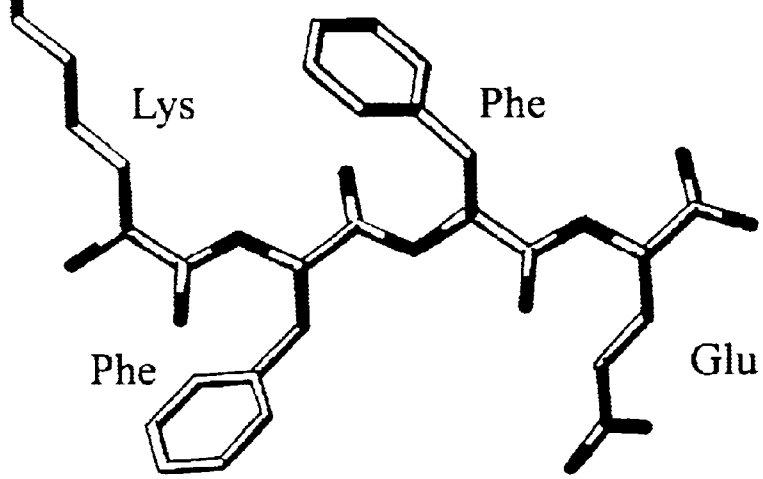
Figure 11A:
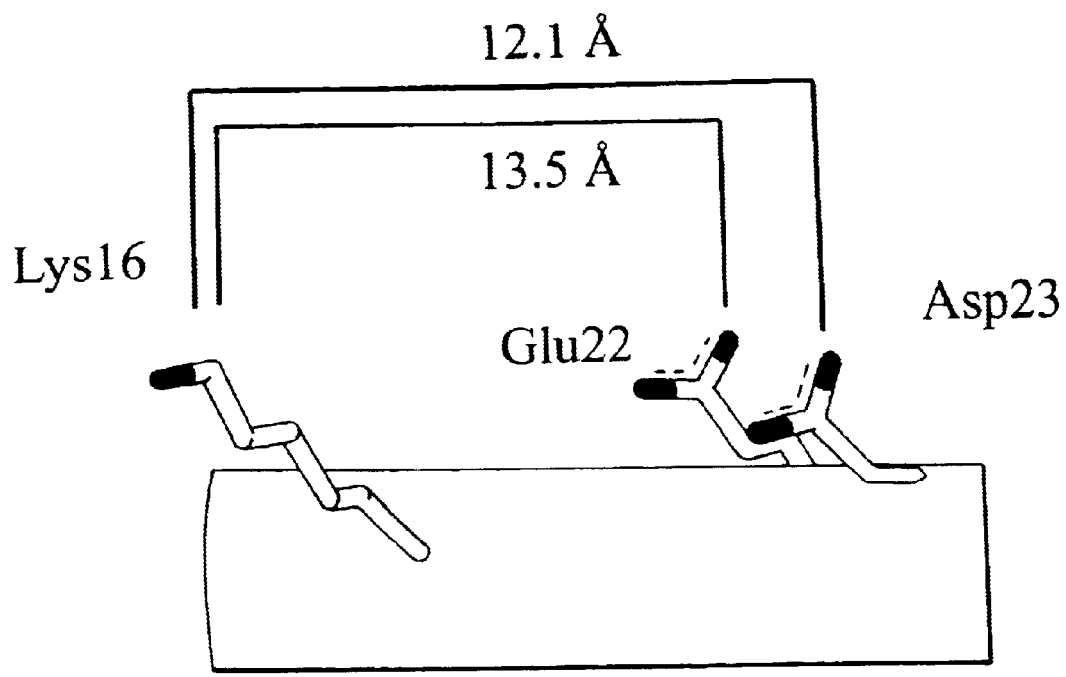
FIG. 11A depicts the charge separation of Aβ (15–23) in α-helical and β-strand conformations. The figure shows the Aβ (15–23) region in helical conformation, symbolized by the cylinder. The charged side-chains Lys16, Glu22 and Asp23 are shown.
Figure 11B:
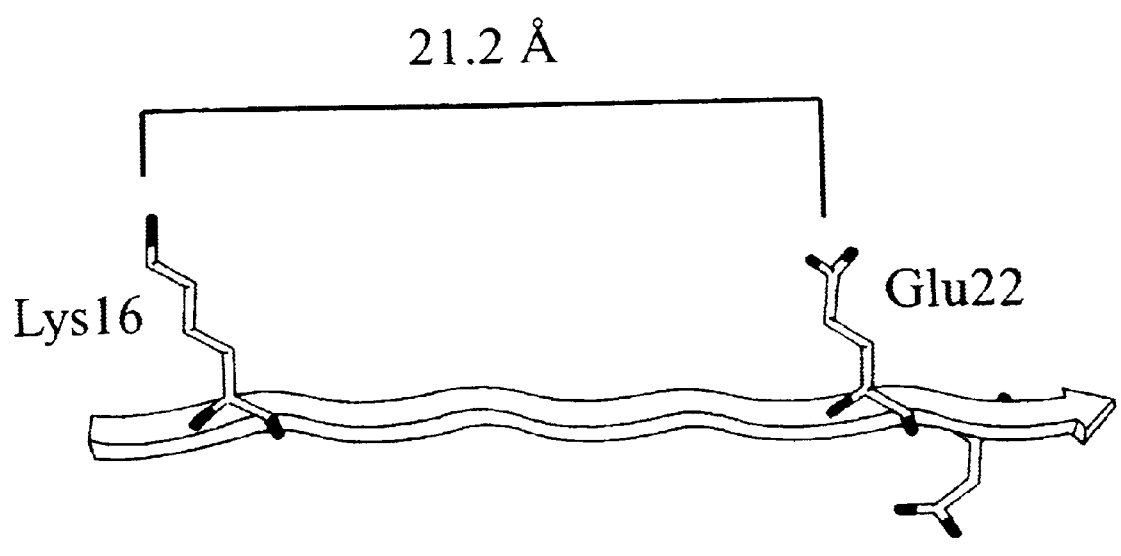
FIG. 11B depicts the charge separation of Aβ(15–23) in α-helical and β-strand conformations. The Aβ(15–23) region is modeled in β-strand/extended conformation, indicated by the wavy strand. The charged side-chains are shown. For the helical conformation, the distances between the ε-amino group of Lys16 and the γ-carboxyl group of Glu22 and the β-carboxyl group of Asp23 are shown, and for the extended conformation the Lys16-Glu22 distance is indicated.

The dipolar KAAE (SEQ ID NO:2) and KFFE (SEQ ID NO:1) did not reduce Aβ fibrillation or aggregation. This was somewhat unexpected considering the similarities to the KAD peptide (the separation of the side-chain charges in KAD in an energy-minimized conformation is 10 Å and the corresponding distance in KFFE is 11 Å). However, the KFFE (SEQ ID NO:1) peptide has a propensity to form a significant portion of β-stranded structure, as detected by a minimum at 215 nm by circular dichroism (CD) spectroscopy, while KAD shows a typical random coil CD spectrum with a minimum only at about 200 nm. The structure of KFFE (SEQ ID NO:1) in extended conformation is shown in FIG. 10, together with the energy-minimized and extended structures of KAD for comparison. The charged side-chains of KAD are separated by 10–11 Å. In contrast, the Lys and Glu side-chains are on opposite sides of the polypeptide backbone in KFFE (SEQ ID NO:1) and no meaningful distance between them can be measured. The relevance of these different charge separations was judged in relation to the charge separations in Aβ. The shortest Aβ peptide investigated herein encompassed residues 14–23 and the smallest helical region detected in this part of Aβ covers residues 15–23. Aβ(15–23) has been found to be helical in the presence of membrane-mimicking solvents or detergents, and forms a β-strand structure in the fibrils. We therefore modeled Aβ(15–23) in α-helical and β-strand conformation (FIG. 11). The separation of side-chain charges of Lys16 and Glu22/Asp23 is 12–13 Å in helical conformation and Lys16 and Glu22 are separated by 21 Å in β-strand conformation, while Lys16 and Asp23 are on opposite sides of the polypeptide backbone. Consequently, the separation of the charged side-chains of KAD, independent of its conformation, is close to the separation of the charges of the side-chains of Lys16 and Glu22/Asp23 in Aβ(15–23) in helical conformation, while the charge separation of KFFE (SEQ ID NO:1) in a conformation that it adopts in solution according to CD measurements does not match the charge separation of Aβ(15–23) in either helical or extended conformation.

---

What is claimed is:

1. A method of identifying a compound that stabilizes an α-helical conformation of a discordant helix in a polypeptide, the method comprising:
   (a) providing a test sample in vitro comprising a polypeptide that contains a discordant helix in the form of an α-helix;
   (b) contacting the test sample with a test compound; and
   (c) determining the rate of decrease in the amount of α-helix in the test sample,
   wherein a lower rate of decrease in the presence of the test compound than in the absence of the test compound is an indication that the test compound stabilizes the α-helical conformation of the discordant helix in the polypeptide.

2. A method of identifying a compound that can stabilize the α-helical conformation of a discordant helix-containing polypeptide, the method comprising:
   (a) providing a test sample in vitro comprising a polypeptide that contains a discordant helix in the form of an α-helix;
   (b) contacting the test sample with a test compound; and
   (c) determining the amount of α-helix present in the test sample,
   wherein a higher amount of α-helix remaining in the presence of the test compound than in the absence of the compound indicates that the test compound stabilizes the α-helical conformation of the discordant helix in the polypeptide.

3. The method of claim 1 or claim 2, wherein the polypeptide that contains a discordant helix is an Aβ peptide.

4. The method of claim 1 or claim 2, wherein the polypeptide that contains a discordant helix is Aβ(1–40).

5. The method of claim 1 or claim 2, wherein the polypeptide that contains a discordant helix comprises residues 14–23 of Aβ peptide.

6. The method of claim 1 or claim 2, wherein the polypeptide that contains a discordant helix comprises residues 16–23 of Aβ peptide.

7. The method of claim 1 or claim 2, wherein the polypeptide that contains a discordant helix is prion protein (PrP) or surfactant associated protein (SP-C).

8. The method of claim 1 or claim 2, wherein the test compound is a peptide.

9. The method of claim 1 or claim 2, wherein the test compound is a tripeptide.

10. The method of claim 1 or claim 2, wherein the test compound is a dipolar tripeptide.

11. The method of claim 1 or claim 2, wherein the test compound is a tetrapeptide.

12. The method of claim 1 or claim 2, wherein the test compound comprises the amino acid sequence KAD.

13. The method of claim 1 or claim 2, wherein the test compound comprises an amino acid sequence selected from the group consisting of KFD, DAK, DFK, RAD, RFD, DAR, DFR, KAE, KFE, EAK, EFK, RAE, RFE, EAR, or EFR.

14. The method of claim 1 or claim 2, wherein the test compound comprises a tripeptide in which the middle residue is an uncharged residue.

15. The method of claim 8, wherein the peptide has protected termini.

16. The method of claim 1 or claim 2, wherein the test compound interacts with Lys16 and Glu22/Asp23 of an Aβ peptide.

17. The method of claim 1 or claim 2, wherein the test compound is a peptidomimetic, small molecule, or antibody.

18. The method of claim 1 or claim 2, wherein the test compound is a monoclonal antibody.

19. The method of claim 1, wherein the rate of decrease in the amount of α-helix in the test sample is determined using electrospray (ES)-mass spectroscopy or matrix-assisted laser desorption/ionization (MALDI) mass spectroscopy.

20. The method of claim 1, wherein the rate of decrease in the amount of α-helix in the test sample is determined using circular dichroism (CD), infrared spectroscopy, Fourier transform infrared spectroscopy (FTIR), or nuclear magnetic resonance (NMR).

21. The method of claim 1, wherein the rate of decrease in the amount of α-helix in the test sample is determined using hydrogen to deuterium (H/D) exchange mass spectroscopy.

22. The method of claim 2, wherein the amount of α-helix in the test sample is determined using electrospray (ES)-mass spectroscopy or matrix-assisted laser desorption/ionization (MALDI) mass spectroscopy.

23. The method of claim 2, wherein the amount of α-helix in the test sample is determined using circular dichroism (CD), infrared spectroscopy, Fourier transform infrared spectroscopy (FTIR), or nuclear magnetic resonance (NMR).

24. The method of claim 2, wherein the amount of α-helix in the test sample is determined using hydrogen to deuterium (H/D) exchange mass spectroscopy.

25. The method of claim 1, further comprising determining the rate of fibril formation in the presence and absence of the test compound.

26. The method of claim 2, further comprising determining the amount of fibril formation in the presence and absence of the test compound.

* * * * *